US009334266B2

(12) United States Patent
Lin

(10) Patent No.: US 9,334,266 B2
(45) Date of Patent: May 10, 2016

(54) CATALYSTS AND RELATED PROCESSES FOR PRODUCING OPTICALLY PURE BETA-LACTONES FROM ALDEHYDES AND COMPOSITIONS PRODUCED THEREBY

(75) Inventor: Yun-Ming Lin, Toledo, OH (US)

(73) Assignee: The University of Toledo, Toledo, OH (US)

( * ) Notice: Subject to any disclaimer, the term of this patent is extended or adjusted under 35 U.S.C. 154(b) by 1102 days.

(21) Appl. No.: 13/393,924

(22) PCT Filed: Jun. 7, 2010

(86) PCT No.: PCT/US2010/037604
§ 371 (c)(1),
(2), (4) Date: Apr. 13, 2012

(87) PCT Pub. No.: WO2011/028309
PCT Pub. Date: Mar. 10, 2011

(65) Prior Publication Data
US 2012/0196740 A1    Aug. 2, 2012

Related U.S. Application Data

(60) Provisional application No. 61/239,963, filed on Sep. 4, 2009.

(51) Int. Cl.
| B01J 31/02 | (2006.01) |
| C07D 305/12 | (2006.01) |
| C07C 227/12 | (2006.01) |
| C07C 67/00 | (2006.01) |
| C07D 205/08 | (2006.01) |
| C07F 15/00 | (2006.01) |
| C07D 453/04 | (2006.01) |

(52) U.S. Cl.
CPC .................................. *C07D 453/04* (2013.01)

(58) Field of Classification Search
None
See application file for complete search history.

(56) References Cited

U.S. PATENT DOCUMENTS

| 3,800,006 A | 3/1974 | Katayama et al. |
| 4,598,089 A | 7/1986 | Hadvary et al. |
| 5,273,995 A | 12/1993 | Roth |
| 5,385,929 A | 1/1995 | Bjorge et al. |
| 5,958,950 A | 9/1999 | Padia et al. |
| 6,011,052 A | 1/2000 | Padia et al. |
| 6,087,511 A | 7/2000 | Lin et al. |
| 6,177,121 B1 | 1/2001 | Elkin et al. |
| 6,184,235 B1 | 2/2001 | Connor et al. |
| 6,476,235 B2 | 11/2002 | Butler et al. |
| 6,605,636 B2 | 8/2003 | Aronhime et al. |
| 6,605,729 B1 | 8/2003 | Byrn et al. |
| 6,646,133 B1 | 11/2003 | Greff et al. |
| 6,933,393 B2 | 8/2005 | Butler |
| 7,144,915 B2 | 12/2006 | Byrn et al. |
| 7,161,012 B2 | 1/2007 | Tessler et al. |
| 7,193,090 B2 | 3/2007 | Guntoori et al. |
| 7,342,120 B2 | 3/2008 | Aronhime et al. |
| 7,361,772 B2 | 4/2008 | Mathew et al. |
| 7,645,888 B2 | 1/2010 | Srinath et al. |
| 7,714,097 B2 | 5/2010 | Zhang et al. |
| 2001/0018427 A1 | 8/2001 | Bisgaier et al. |
| 2002/0028833 A1 | 3/2002 | Booth et al. |
| 2003/0162827 A1 | 8/2003 | Venkataram et al. |
| 2003/0212279 A1 | 11/2003 | Tessler et al. |
| 2004/0220254 A1 | 11/2004 | Nelson et al. |
| 2005/0038007 A1 | 2/2005 | Curatolo et al. |
| 2005/0239869 A1 | 10/2005 | Butler et al. |
| 2005/0261359 A1 | 11/2005 | Tessler et al. |
| 2005/0271717 A1 | 12/2005 | Berchielli et al. |
| 2006/0128971 A1 | 6/2006 | Turchetta et al. |
| 2006/0142592 A1 | 6/2006 | Finkelstein |
| 2006/0205804 A1 | 9/2006 | Nelson et al. |
| 2006/0211761 A1 | 9/2006 | Kumar et al. |
| 2006/0229363 A1 | 10/2006 | Hamanaka |
| 2006/0241169 A1 | 10/2006 | Park |
| 2006/0252816 A1 | 11/2006 | Wang et al. |
| 2007/0032662 A1 | 2/2007 | Butler et al. |
| 2007/0166360 A1 | 7/2007 | Nakai et al. |
| 2009/0030172 A1 | 1/2009 | Zheng et al. |
| 2009/0047687 A1 | 2/2009 | Lowe et al. |
| 2009/0203944 A1 | 8/2009 | An et al. |
| 2009/0226510 A1 | 9/2009 | Berchielli et al. |
| 2010/0048899 A1 | 2/2010 | Dandala et al. |

FOREIGN PATENT DOCUMENTS

WO    2008077560 A1    7/2008

OTHER PUBLICATIONS

Chidara et al. Synlett, 2009, 1675.*
Nielsen et al. JACS, 2004, 126, 1360-1362.*
Hutson et al. Organic Letters, 2007, 9(20), 3869-3872.*
Romo et al., "Synthesis and Inhibitory Action on HMG-CoA Synthase of Racemic and Optically Active Oxentan-2-ones (β-Lactones)", Bioorganic & Medicinal Chemistry, 1998, vol. 6, pp. 1255-1272.
Extended European Search Report, Application No. 10814107.8 dated Oct. 28, 2013.
Supplementary European Search Report, Application No. 10814107.8 dated Nov. 14, 2013.
European Examination Report, Application No. 10814107.8 dated Jul. 29, 2014.
Adamus, G. et al., "Anionic Ring-Opening Polymerization of Beta-Alkoxymethyl-Substituted Beta-Lactones," Biomacromolecules, 2008, pp. 696-703, vol. 9, Abstract only.
Casarotto, V. et al., "Design and Synthesis of a Tridentate Ligand for Asymmetric Bifunctional Catalysis," Tetrahedron Letters, 2007, pp. 5561-5564, vol. 48.

(Continued)

*Primary Examiner* — Yun Qian
(74) *Attorney, Agent, or Firm* — MacMillan, Sobanski & Todd, LLC

(57) ABSTRACT

Bi-functional cobalt-containing catalysts useful for making stereo specific compounds and compositions, along with methods of making, and uses thereof in the syntheses of optically pure β-lactones from aldehydes and ketene are described. Precursors, intermediates, compositions, and particular features of the use if the compositions, such as high enantiomeric selectivity, high yield and low mole percent of catalyst useful are provided.

2 Claims, 8 Drawing Sheets

(56) References Cited

OTHER PUBLICATIONS

Chidara, S. et al., "Reaction Rate Acceleration Enabled by Tethered Lewis Acid-Lewis Base Bifunctional Catalysis: A Catalytic, Enantioselective [2+2] Ketene Aldehyde Cycloaddition Reaction," Synlett, 2009, pp. 1675-1679, No. 10.

Chaplin, A.J. et al., "Use of Betapropiolactone to Disinfect Fresh Tissue Without Impairing Antigenicity: Method Applicable to Human Immunodeficiency Virus (HIV) Positive Tissue," J Clin Pathol., Mar. 1989, pp. 318-321, vol. 42.

Frunza, L. et al., "Embedding Jacobsen Manganese (III) Salen Complex into Nanoporous Molecular Sieves: Spectroscopic Characterisation of Hose-Guest-Interactions," Journal of Optoelectronics and Advanced Materials, Aug. 2005, pp. 2141-2148, vol. 7, No. 4.

Gnanadesikan, V., et al., "Enantioselective Beta-Lactone Formation from Ketene and Aldehydes Catalyzed by a Chiral Oxazaborolidine," Organic Letters, 2006, pp. 4943-4945, vol. 8, No. 21.

Hoffman, R.K. et al., "Beta-Propiolactone Vapor as a Disinfectant," 57th General Meeting of the Society of American Bacteriologists, Detroit, Michigan, Apr. 1957, pp. 358-362.

Katona, S.J. et al., "Effect of Beta Propiolactone Viral Inactivation on α1 Antitrypsin Values," J Clin Pathol., 2002, pp. 659-5534, vol. 48.

Lin, Y.-M., "316 Tethered Lewis Acid-Lewis Base Asymmetric Bifunctional Catalysis: Reaction Rate Acceleration and a New Catalytic Aldehyde Olefination Reaction," Central Regional Meeting of the American Chemical Society, Cleveland, Ohio, May 2009, Abstract.

Lin, Y.-M. et al., "A Catalytic, Highly Stereoselective Adlehyde Olefination Reaction," Tetrahedron Letters, 2007, pp. 5531-5534, vol. 48.

Lin, Y.-M. et al., "A Lewis Acid-Lewis Base Bifunctional Catalyst from a New Mixed Ligand," Organic Letters, 2007, pp. 567-570, vol. 9, No. 4.

Lin, Y.-M., "Asymmetric Morita-Baylis-Hillman Reaction: A Novel Tethered Bifunctional Lewis Acid-Lewis Base Catalysis Strategy," 52nd Annual Report on Research Under Sponsorship of the ACS Petroleum Research Fund, 2007 Annual Report, Abstract.

Lin, Y.-M. et al., "Predicting the R/S Absolute Configeration in Asymmetric Bifunctional Catalysis (ABC)," Tetrahedron Letters, 2007, pp. 5275-5278, vol. 48.

Liu, X.-Q. et al., "Synthesis and Ring-Opening Polymerization of α-chloromethyl-α-methyl-β-propriolactone," Macromol. Chem. Phys., 1999, pp. 468-473, vol. 200.

Nelson, S.G. et al., "Catalyzed Acyl Halide-Aldehyde Cyclocondensations. New Insights into the Design of Catalytic Cross Aldol Reactions," Tetrahedron Letters, 1999, pp. 6535-6539, vol. 40.

Nelson, S.G. et al., "Catalytic Asymmetric Acyl Halide-Aldehyde Cyclocondensation Reaction," Organic Synthesis, 2005, pp. 170-174, vol. 82.

Nelson, S.G. et al., "Sn2 Ring Opening of β-Lactones: An Alternative to Catalytic Asymmetric Conjugate Additions," J. Org. Chem., 2002, pp. 4680-4683, vol. 67.

Schwindt, M.A. et al., "Enantioselective Synthesis of a Key Intermediate in a New Process for Orlistat Using Asymmetric Hydrogenation and a Grignard Reagent Promoted Lactone Cyclization," Organic Process Research & Development, 2007, pp. 524-533, vol. 11.

Shkidchenko, A.N. et al., "Bactericidal Action of β-Propiolactone Homologue," Process Biochemistry, Jul. 2004, pp. 1465-1468, vol. 30, Issue 11 Abstract only.

Spectrum Laboratories: Chemical Fact Sheet—Case #57578, www.speclab.com/compound/c57578.htm, Retrieved from Web: May 21, 2010, pp. 1-2.

The Independent Research Group, Chiral Quest, Inc., Oct. 10, 2003, pp. 1-30.

Yang, H.W. et al., "Methods for the Synthesis of Optically Active β-Lactones (2-Oxetanones)," Tetrahedron, 1999, pp. 6403-6434, vol. 55.

PCT International Preliminary Report of Patentability, PCT/US10/037604 filed Jun. 7, 2010, dated Mar. 15, 2012.

PCT International Search Report and Written Opinion, PCT/US10/037604 filed Jun. 7, 2010, dated Aug. 9, 2010.

\* cited by examiner

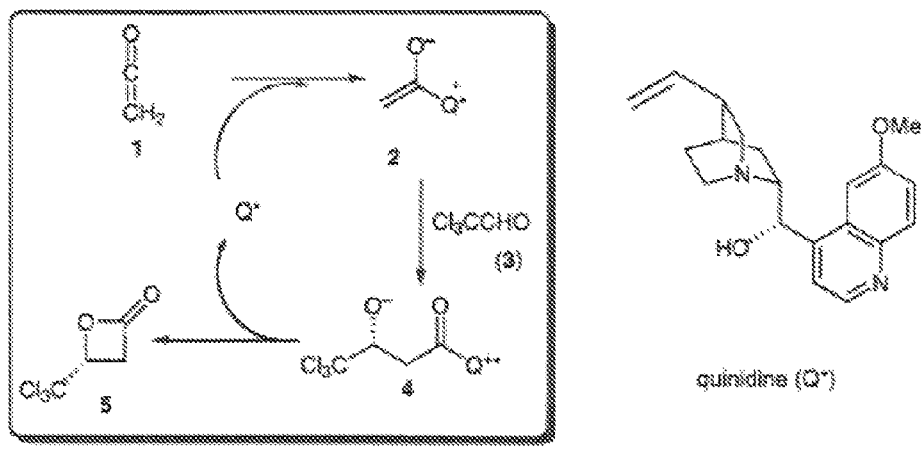
FIGURE 1 - Scheme 1 - Prior Art
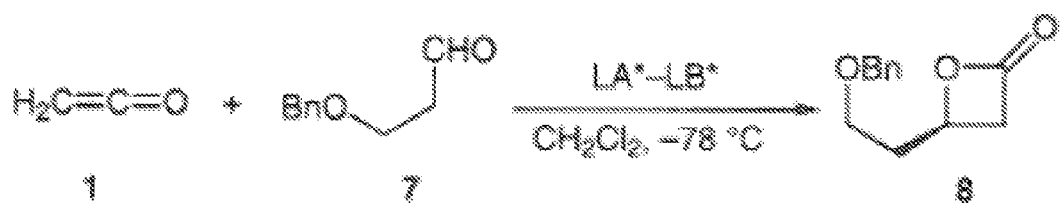
FIGURE 2 - Scheme 2
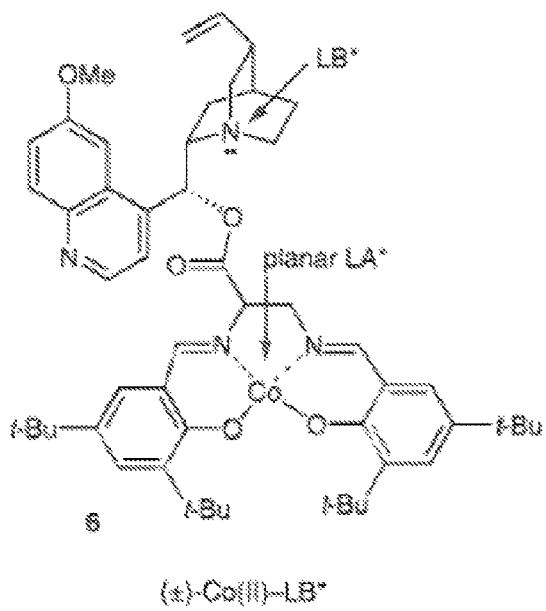
FIGURE 3A - Prior Art

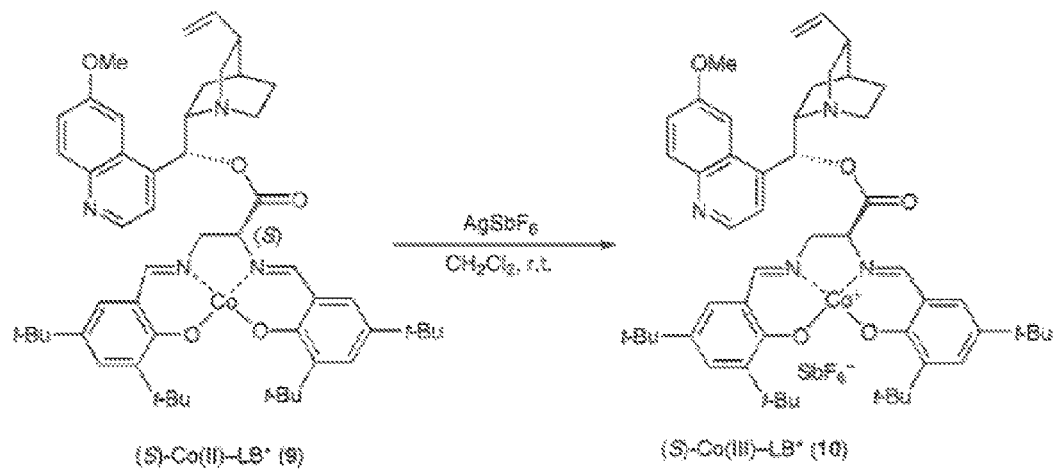
FIGURE 3B - Scheme 3
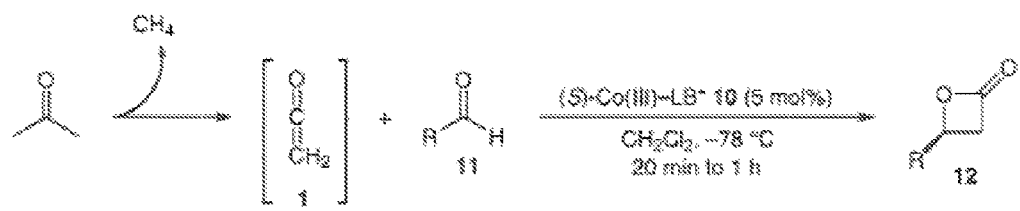
FIGURE 4 - Scheme 4
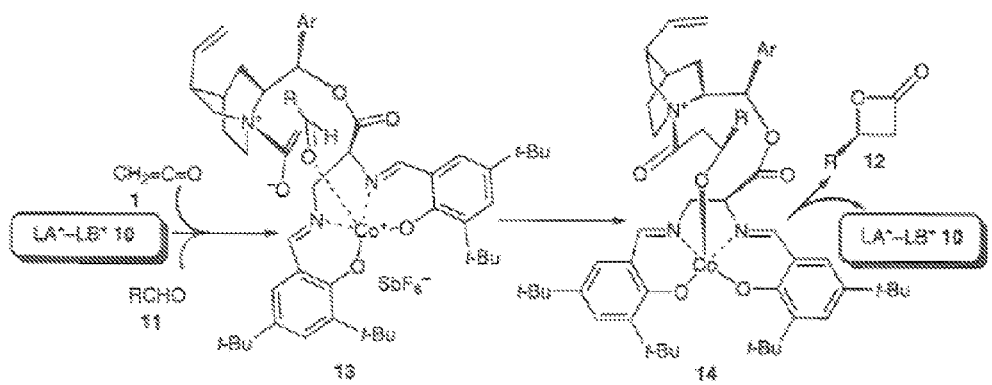
FIGURE 5 - Scheme 5

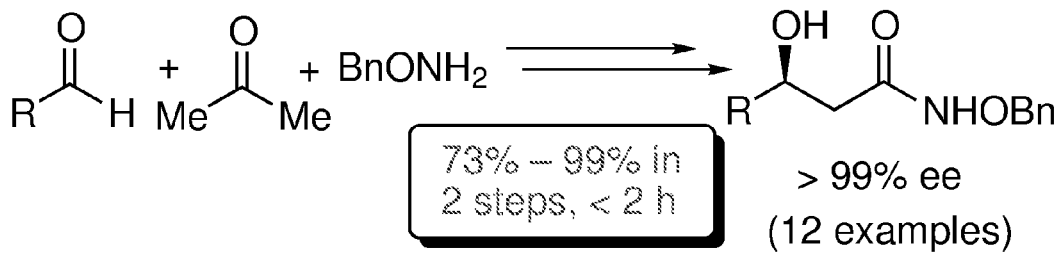
FIGURE 6 - Scheme 6
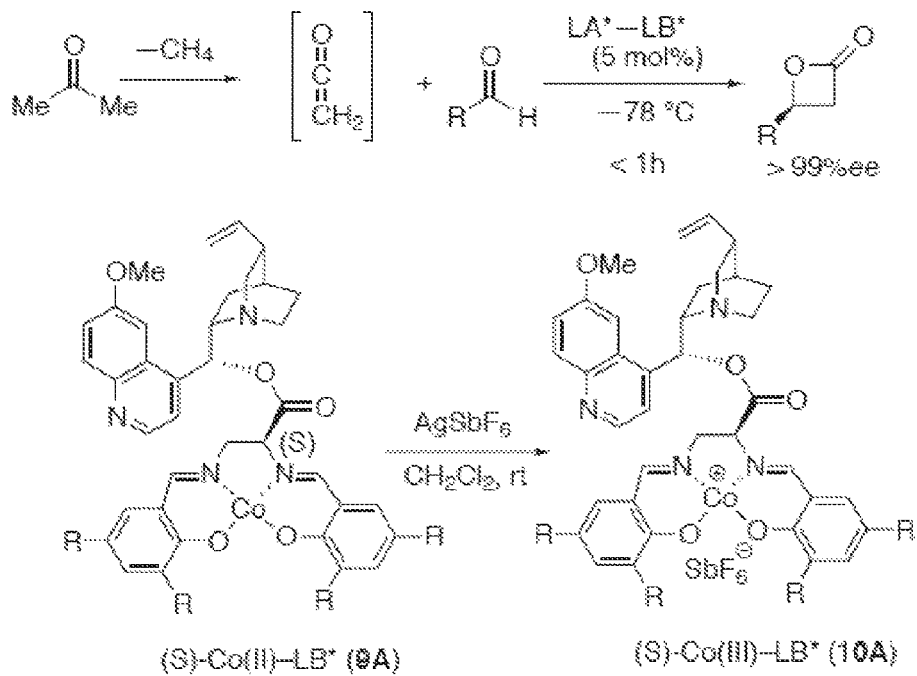
FIGURE 7 - Scheme 7
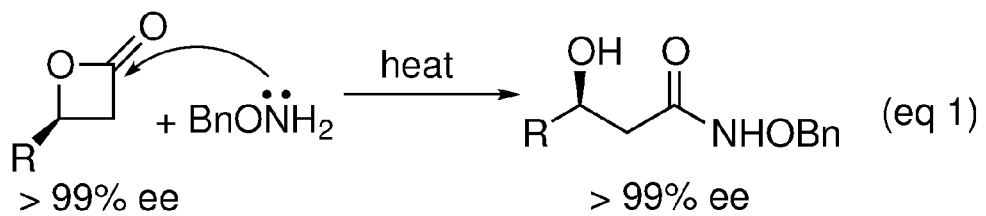
FIGURE 8 - Scheme 8

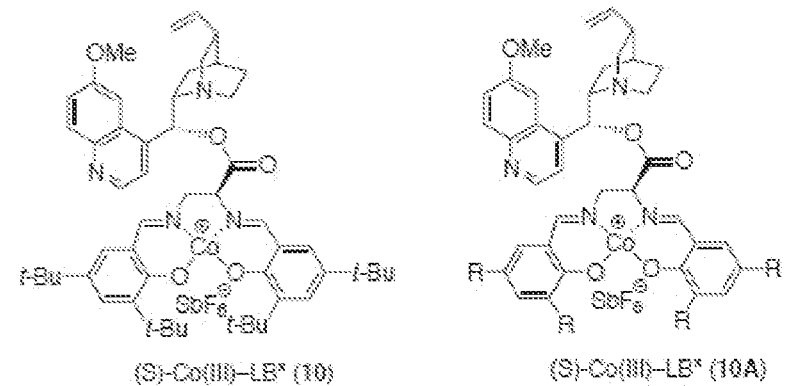
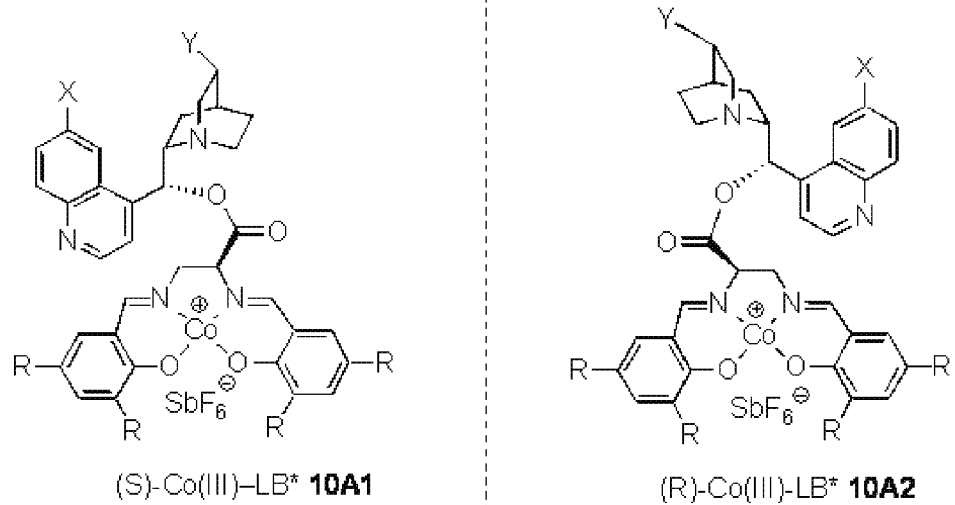
Figure 10

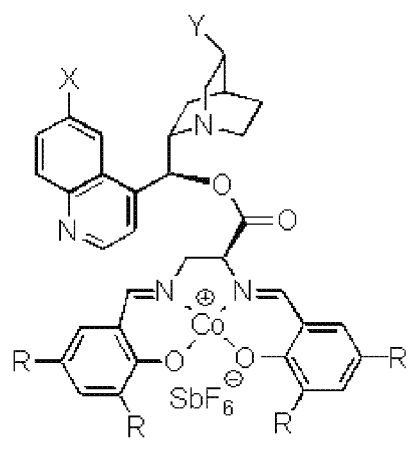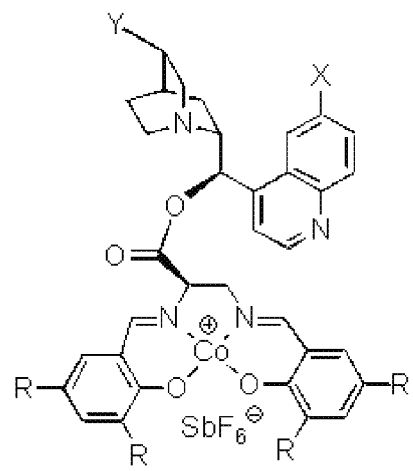
(S)-Co(III)-LB* 12A1    (R)-Co(III)-LB* 12A2
(Pseudo mirror image of 12A1)
Mirror
Figure 12

US 9,334,266 B2

CATALYSTS AND RELATED PROCESSES FOR PRODUCING OPTICALLY PURE BETA-LACTONES FROM ALDEHYDES AND COMPOSITIONS PRODUCED THEREBY

CROSS-REFERENCE TO RELATED APPLICATIONS

This application is filed under 35 U.S.C. §371 as a U.S. National Phase application which claims priority under 35 U.S.C. §119, 35 U.S.C. §120, the Patent Cooperation Treaty and/or all applicable authority to: PCT/US2010/037604 filed under the authority of the Patent Cooperation Treaty on Jun. 7, 2010, published; which claims priority to U.S. Provisional Application Ser. No. 61/239,963 filed under 35 U.S.C. §111 (b) on Sep. 4, 2009; the disclosures of all priority applications are incorporated herein by reference.

STATEMENT REGARDING SPONSORED RESEARCH

This invention was made with government support under Grant number NSF (CHE-0829263). The government has certain rights in this invention.

FIELD OF INVENTION

In a broad aspect, the present invention relates to a catalyst compound and methods and uses thereof in the syntheses of optically pure β-lactones from aldehydes and ketene via a catalytic method.

BACKGROUND OF THE INVENTION

There is no admission that the background art disclosed in this section legally constitutes prior art.

Enantiomerically pure β-lactones are valuable small molecules that can be converted into a variety of chiral synthons for asymmetric synthesis.[1] Because the [2+2] cycloaddition reaction between ketene and aldehydes affords β-lactones in one step, developing new catalytic methods for synthesizing β-lactones from ketene and aldehydes attracts much attention.[1,2]

Quinidine-based catalysts. FIG. 1-Scheme 1 shows the enantioselective synthesis of β-lactone 5 from ketene 1 and chloral 3, catalyzed by quinidine (Q*).[3] This formal [2+2] reaction entails a tandem aldol-lactonization process (from 2 to 4 to 5) to produce the β-lactone 5 in highly desirable enantiomeric purity (ee), but limited only to activated substrates. Significant research effort has been devoted to expanding the substrate scope of the [2+2] reaction.

Other catalysts. In addition to strategies for synthesizing bi-cyclic β-lactones from aldehyde acids,[4] others have developed new catalytic methods to synthesize chiral β-lactones from aldehydes and substituted ketenes.[5] Also, chiral Lewis bases (LB*) and chiral Lewis acids (LA*) were developed to synthesize β-lactones from pure ketenes.[6a,6b] Most recently, new catalytic systems have been developed for the [2+2] cycloaddition reaction between aldehydes and substituted ketenes.[6c,6d,6e]

Lewis acid-Lewis base (LA*-LB*) bi-functional Co(II) catalysts. The inventor herein previously synthesized a (±)-Co(II)-LB bi-functional catalyst 6 from the (±)-diaminopropionic acid, and demonstrated the LB*-dependent asymmetric induction concept.[7,9] The present inventor previously used a CoII-based bifunctional catalyst in a [2+2] cycloaddition reaction as a test reaction (FIG. 3A).[7] The inventor herein also previously developed an empirical model for predicting the R/S absolute stereochemistry of LA*-LB* catalyzed reactions.[9]

Described herein is a further development by the inventor that provides valuable chiral compositions and processes for producing them.

SUMMARY OF THE INVENTION

Until the inventor's discovery (which forms the basis of at least a part of the present invention), no catalysts or catalytic methods that rapidly produce enantiomerically pure (i.e., >99% ee) C4-alkyl or aryl β-lactones are currently available for the [2+2] cycloaddition reaction between aldehydes and unsubstituted ketene.

Part I

In a first broad aspect, there are provided herein chiral compositions that are valuable as chiral building blocks, and processes for producing them.

In particular, such compositions are useful as precursors for manufacturing marketed drugs by the biotech, chemical, and pharmaceutical industries.

Also, in a particular aspect, the process includes producing optically pure β-lactones from aldehydes and compositions produced thereby.

In a non-limiting example, highly enantioselective [2+2] reaction that displays remarkable rate acceleration. In a particular embodiment, the reaction is catalyzed by a Co(III)-based LA*-LB* bi-functional catalyst.

In another broad aspect, there is provided herein a bi-functional catalyst that promotes the rapid formation of β-lactones from aldehydes and ketenes. In certain embodiments, the reaction times ranges from mere minutes to an hour or less.

In particular, there is provided herein a tethered LA*-LB* bi-functional catalyst that is especially useful in the formation of enantiomerically pure (>99% ee) β-lactones rapidly from aldehydes and ketenes.

In another aspect, C4-monosubstituted β-lactones are produced in high yields having unprecedented reaction time efficiency.

In one embodiment, the catalyst compound is useful for a catalytic, enantioselective [2+2] cycloaddition reaction between aldehydes and substituted and unsubstituted ketenes with high reaction rate acceleration and stereoselectivity.

Part II

In another aspect, there is provided herein a method for making a substantially optically pure hydroxamate aldol.

In another aspect, there is provided herein use of one or more β-lactone compounds as a substantially optically pure chiral compound for forming at least one of: β-lactams, and β-amino acids.

Part III
Also provided are compounds of the Formula I

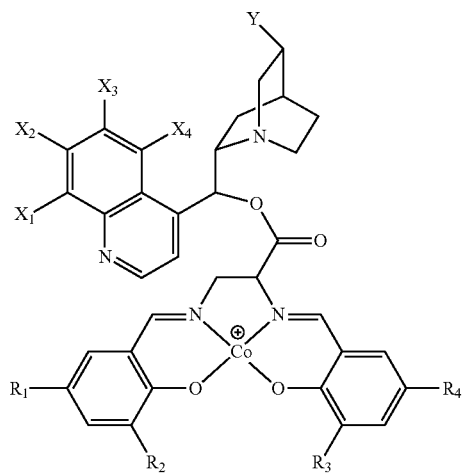

Formula I wherein one of X1 through X4 is alkoxy, alkyl, or a linker and the remaining three are hydrogen; Y is alkyl, alkenyl, or alkynyl; and R1 through R4 are independently alkyl (C3-10) or silyl.

Compositions comprising the compounds are also provided. In particular, there are provided compositions comprising the compounds and at least one counterion.

Also provided are compositions of matter comprising Formula I,

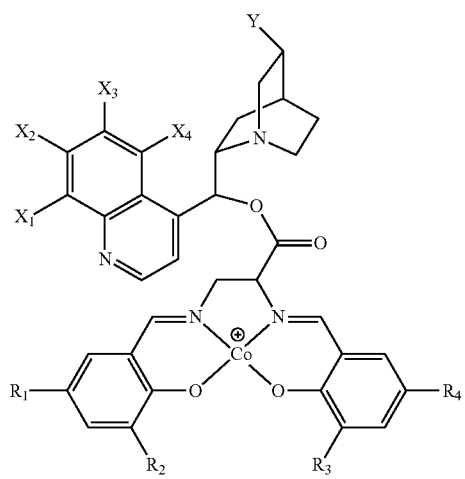

Formula I wherein one of X1 through X4 is O-methyl, or vinyl and the remaining three are hydrogen; Y is vinyl; and R1 through R4 are isopropyl or t-butyl; and wherein the composition further comprises at least one counterion. In particular, compositions wherein the counterion is selected from the group consisting of: SbF6- and BF4- are provided.

Also provided are compositions of matter comprising Formula I,

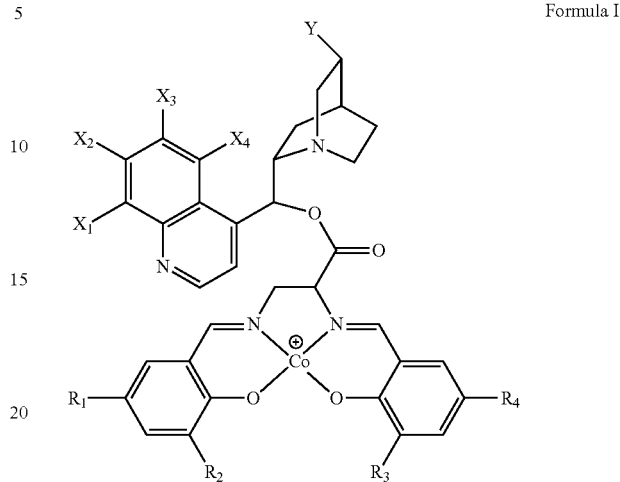

Formula I wherein X1, X2 and X4 are hydrogen; X3 is O-methyl; Y is vinyl; R1 through R4 are each t-butyl; and wherein the composition further comprises at least one SbF6-counterion. In particular, compositions are provided which comprise at least about 85%, at least about 90%, at least about 95%, at least about 99%, of a single stereoisomer of a compound herein, wherein the percentage is relative to the total stereoisomers of compounds in the composition. In particular, there are provided stereoisomers as depicted in a figure selected from the group consisting of: FIG. 10A1; FIG. 10A2; FIG. 11A1; FIG. 11A2; FIG. 12A1; FIG. 12A2; FIG. 13A1; FIG. 13A2.

In particular, there are provided compounds of the formula and stereochemistry shown in the following eight Formulas, wherein one of X1 through X4 is alkoxy, alkyl, or a linker and the remaining three are hydrogen; Y is alkyl, alkenyl, or alkynyl; and R1 through R4 are alkyl (C3-10) or silyl; or wherein one of X1 through X4 is O-methyl or vinyl and the remaining three are hydrogen; Y is vinyl; and R1 through R4 are isopropyl or t-butyl; or wherein X1, X2 and X4 are hydrogen; X3 is O-methyl; Y is vinyl; R1 through R4 are each t-butyl:

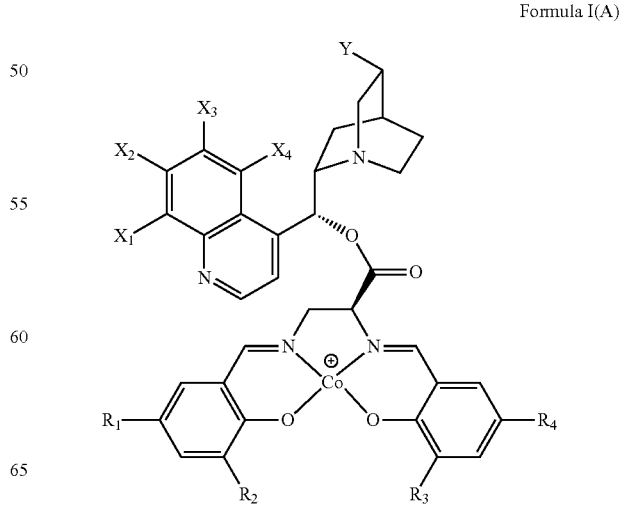

Formula I(A)

-continued
Formula I(B)
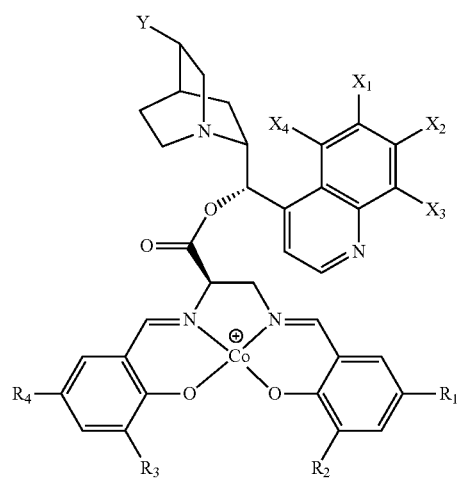
Formula I(C)
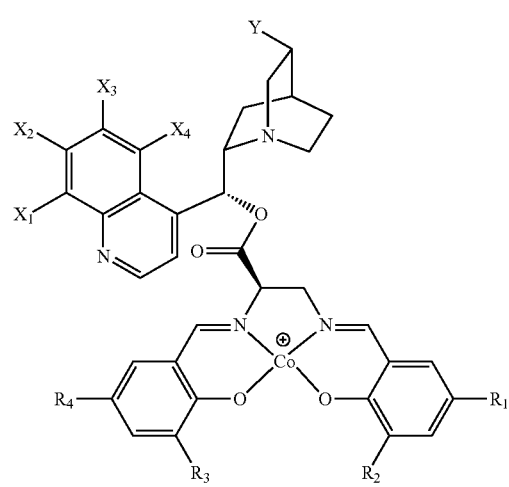
Formula I(D)
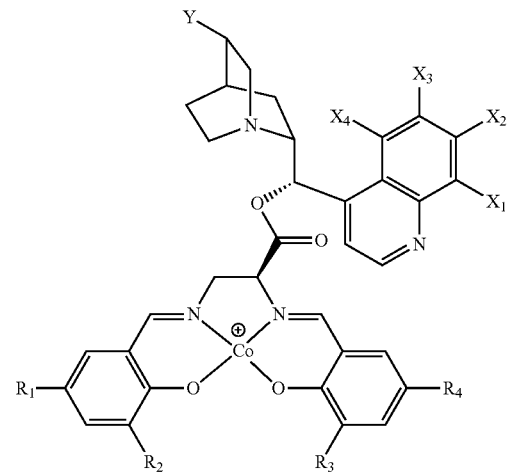
Formula I(E)
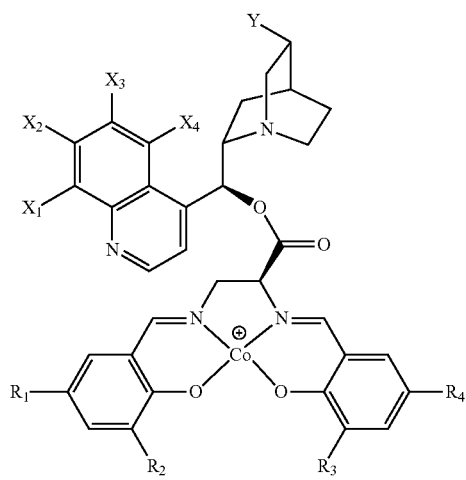
Formula I(F)
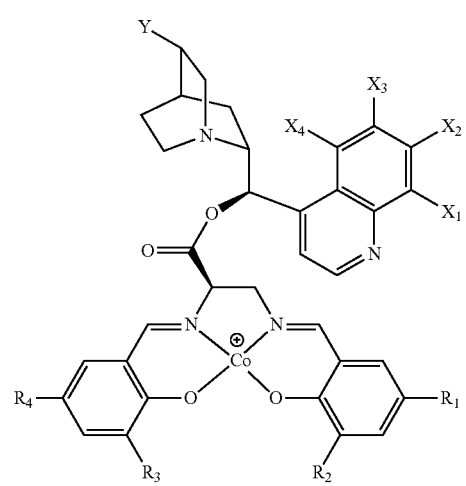
Formula I(G)
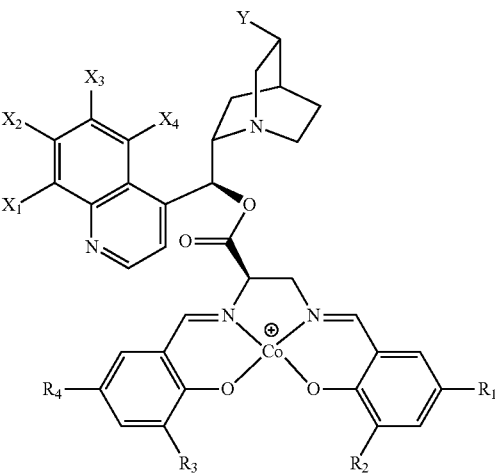

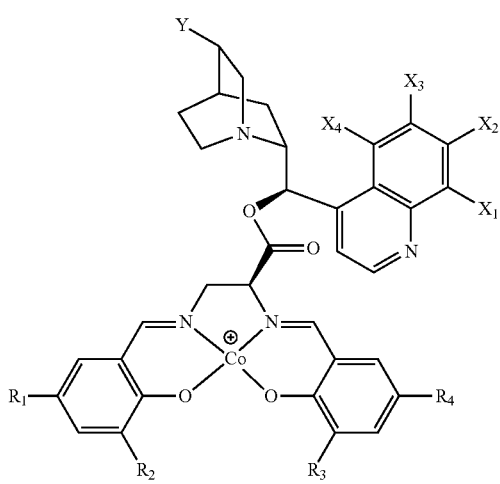

Formula I(H)

Also provided are compositions of any of the above, which further comprise an unoxidized precursor of Formula I having Formula II

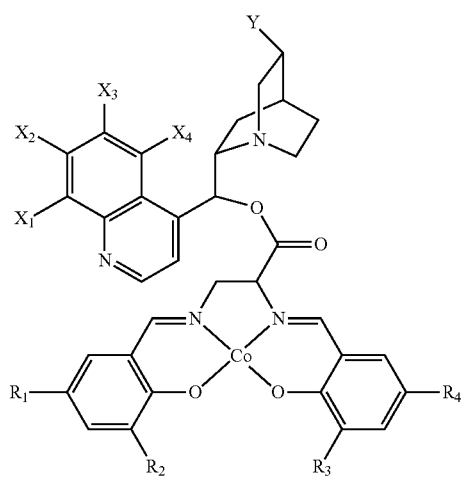

Formula II wherein one of X1 through X4 is alkoxy, alkyl, or a linker and the remaining three are hydrogen; Y is alkyl, alkenyl, or alkynyl; and R1 through R4 are alkyl (C3-10) or silyl; or wherein one of X1 through X4 is O-methyl or vinyl and the remaining three are hydrogen; Y is vinyl; and R1 through R4 are isopropyl or t-butyl; or wherein X1, X2 and X4 are hydrogen; X3 is O-methyl; Y is vinyl; R1 through R4 are each t-butyl.

Compositions are provided which comprises at least one stereoisomer and at least one counterion.

Also provided are compositions as described, which further comprise an unoxidized precursor of Formula I having Formula II

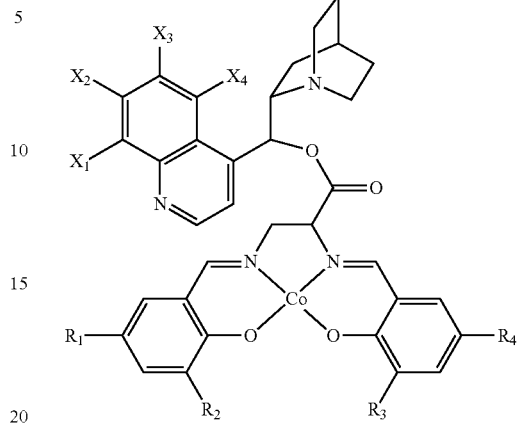

Formula II wherein one of X1 through X4 is alkoxy, alkyl, or a linker and the remaining three are hydrogen; Y is alkyl, alkenyl, or alkynyl; and R1 through R4 are independently alkyl (C3-10) or silyl.

Also provided are compositions as described which further comprises an unoxidized precursor of Formula I having Formula II

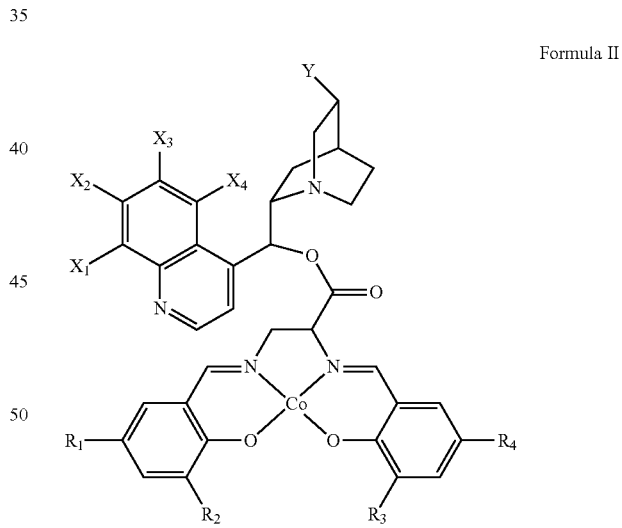

Formula II wherein one of X1 through X4 is O-methyl, or vinyl and the remaining three are hydrogen; Y is vinyl; and R1 through R4 are isopropyl or t-butyl.

Also provided are compositions as described, which further comprise an unoxidized precursor of Formula I having Formula II Formula II

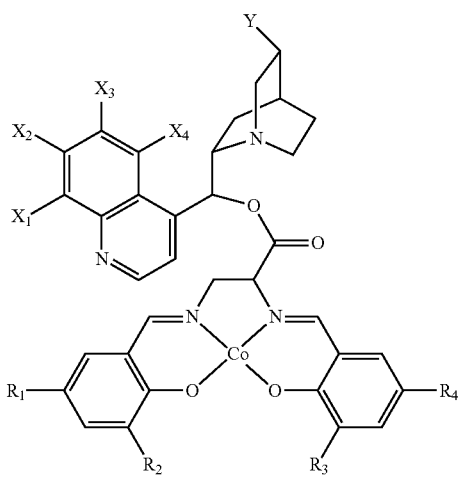

wherein X1, X2 and X4 are hydrogen; X3 is O-methyl; Y is vinyl; and R1 through R4 are each t-butyl.

Also provided are any of the compositions herein which further comprise an oxidant. In particular provided are compositions wherein the oxidant is selected from the group consisting of: AgSbF6 and AgBF4. Specifically provided are compositions wherein the oxidant is AgSbF6.

Also provided are compositions wherein the compound is present at from about 0.01 mole percent to about 10 mole percent, from about 0.1 mole percent to about 5 mole, from about 0.05 mole percent to about 1 mole percent, and about 0.5 mole percent.

Also provided are compositions herein which further comprise a medium comprising at least one composition selected from the group consisting of: solvent; polymer; desiccant; cell; mineral; carbohydrate.

Also provided are compounds of the Formula II

Formula II

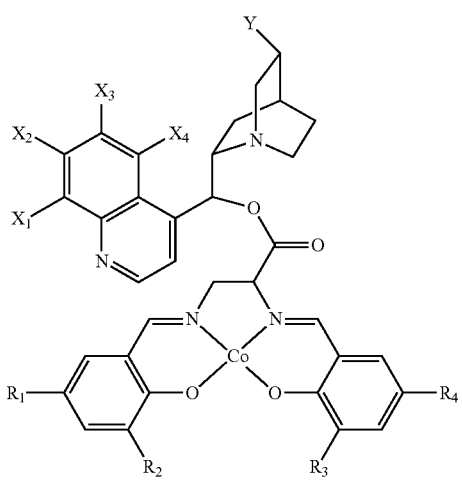

wherein one of X1 through X4 are alkyl and the remaining three are hydrogen; Y is hydrogen, alkoxy, alkyl, or a linker; Y is alkyl, alkenyl, or alkynyl; and R1 through R4 are alkyl (C3-10) or silyl, or stereoisomers thereof.

Also provided are compounds of the Formula II (A)

Formula II(A)

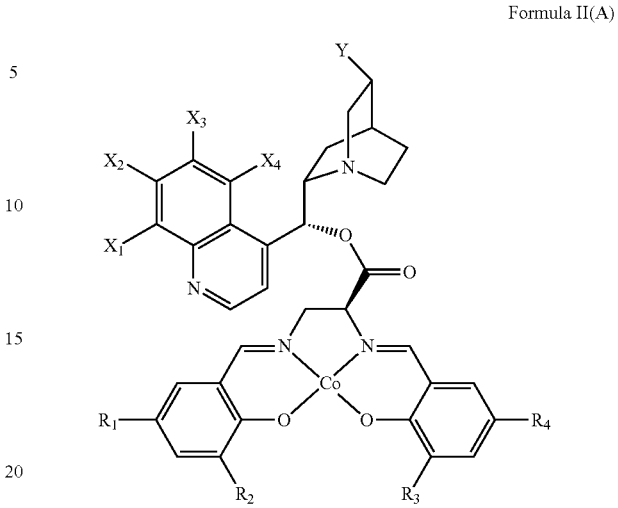

wherein one of X1 through X4 are alkyl and the remaining three are hydrogen; Y is hydrogen, alkoxy, alkyl, or a linker; Y is alkyl, alkenyl, or alkynyl; and R1 through R4 are alkyl (C3-10) or silyl; or
wherein one of X1, X2, and X4 is alkoxy and the other two are hydrogen; X3 is hydrogen; Y is alkyl (C3-10); and R1 through R4 are alkyl (C3-10) or silyl; or
wherein X1, X2 and X4 are each hydrogen; X3 is vinyl; Y is vinyl; and R1 through R4 are isopropyl or t-butyl.

Also provided are compounds of the following Formulas II(B) through Formula II(H), wherein one of X1 through X4 is alkoxy, alkyl, or a linker and the remaining three are hydrogen; Y is alkyl, alkenyl, or alkynyl; and R1 through R4 are alkyl (C3-10) or silyl; or
wherein one of X1 through X4 is O-methyl or vinyl and the remaining three are hydrogen; Y is vinyl; and R1 through R4 are isopropyl or t-butyl; or
wherein X1, X2 and X4 are hydrogen; X3 is O-methyl; Y is vinyl; R1 through R4 are each t-butyl: wherein one of X1 through X4 are alkyl and the remaining three are hydrogen; Y is hydrogen, alkoxy, alkyl, or a linker; Y is alkyl, alkenyl, or alkynyl; and R1 through R4 are alkyl (C3-10) or silyl; or
wherein one of X1, X2, and X4 is alkoxy and the other two are hydrogen; X3 is hydrogen; Y is alkyl (C3-10); and R1 through R4 are alkyl (C3-10) or silyl; or
wherein X1, X2 and X4 are each hydrogen; X3 is vinyl; Y is vinyl; and R1 through R4 are isopropyl or t-butyl.

Formula II(B)

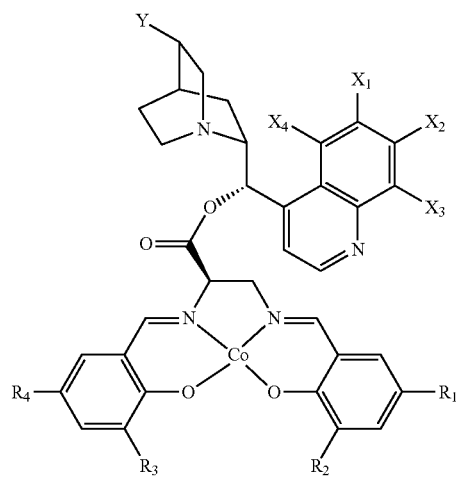

Formula II(C)
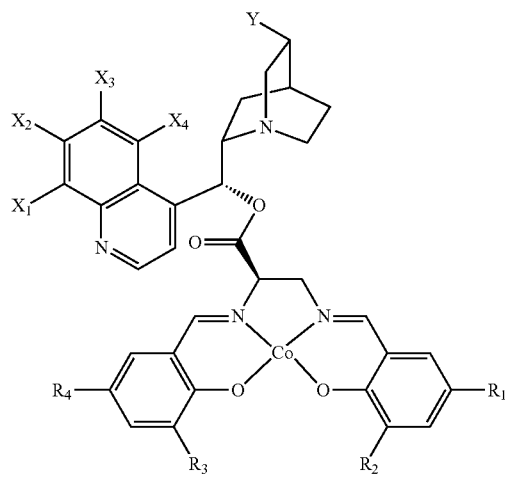
Formula II(D)
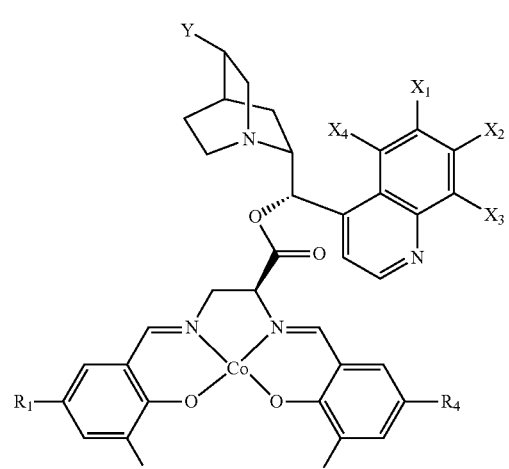
Formula II(E)
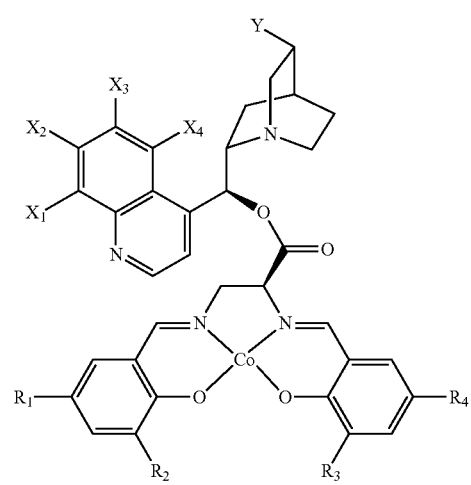
Formula II(F)
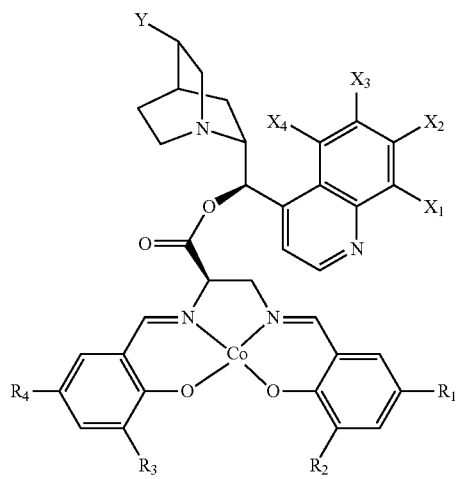
Formula II(G)
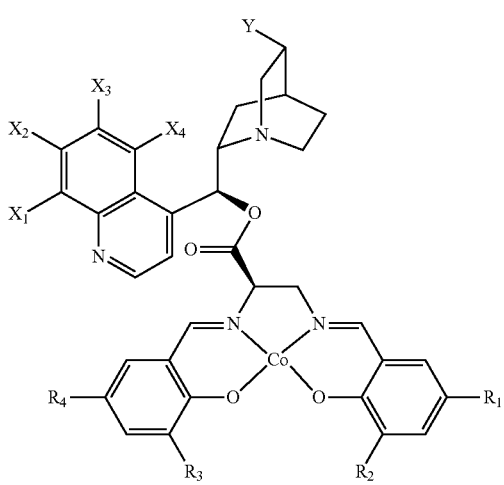
Formula II(H)
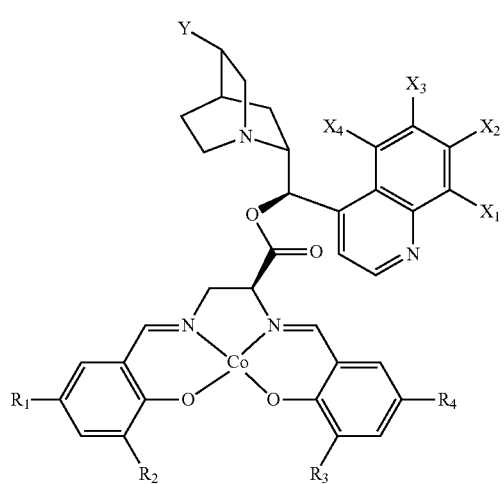

Also provided are methods to make a compound of Formula II

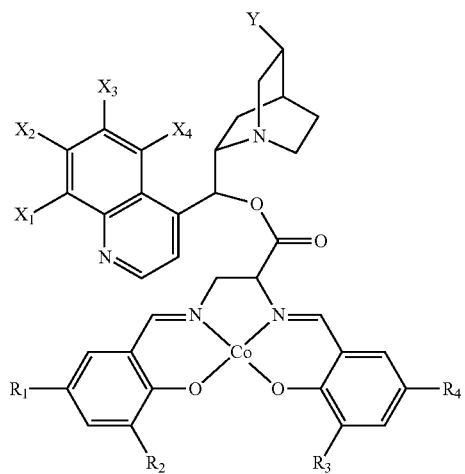

Formula II wherein one of X1 through X4 is alkoxy, alkyl, or a linker and the remaining three are hydrogen; Y is alkyl, alkenyl, or alkynyl; and R1 through R4 are independently alkyl (C3-10) or silyl, comprising: dissolving an anhydrous cobalt salt in a solution of salen ligand.

Also provided are those methods as described which further comprise a step of purifying the resulting Co(II)-salen complex.

Also provided are methods to make a compound of Formula II

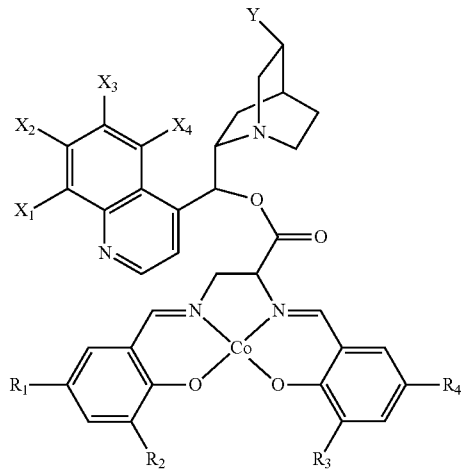

Formula II wherein one of X1 through X4 is alkoxy, a linker, or vinyl and the remaining three are hydrogen; Y is alkyl, alkenyl, or alkynyl; and R1 through R4 are independently alkyl (C3-10) or silyl, comprising:
  a.) dissolving salen ligand in solvent;
  b.) degassing the solution of step a.)
  c.) dissolving anhydrous cobalt salt in the solution of step b.)
  d.) removing the solvent of step a.) so as to produce a concentrated solution; and
  e.) adding degassed pentane to the concentrated solution of step d.) so as to precipitate a compound of Formula II.

Also provided are methods wherein the salen ligand comprises quinine and/or quinidine.

Also provided are methods wherein step d.) is accomplished by distillation.

Also provided are methods which further comprise, after step c.), a step of refluxing the solution.

Also provided are methods wherein the solution is refluxed for at least approximately one hour, and not more than approximately twelve hours; or at least approximately two hours, and not more than approximately five hours.

Also provided are methods herein which further comprise a step of oxidizing the compound of Formula II to produce an oxidized Formula II compound.

Also provided are methods herein wherein the oxidation is accomplished via the use of an oxidant selected from the group consisting of: AgSbF6 and AgBF4.

Also provided are methods herein wherein oxidation is accomplished via the use of SbF6.

Also provided are methods herein wherein the resulting oxidized Formula II compound comprises of at least 90%, at least 95%, and at least 98% of one particular stereoisomer.

Also provided are methods herein wherein the method results in a yield of oxidized Formula II compound of at least 90% and at least 95%.

Products made by the present processes/methods are also provided herein.

Also provided are methods to make oxidized COII compounds herein, comprising oxidizing a compound of Formula II

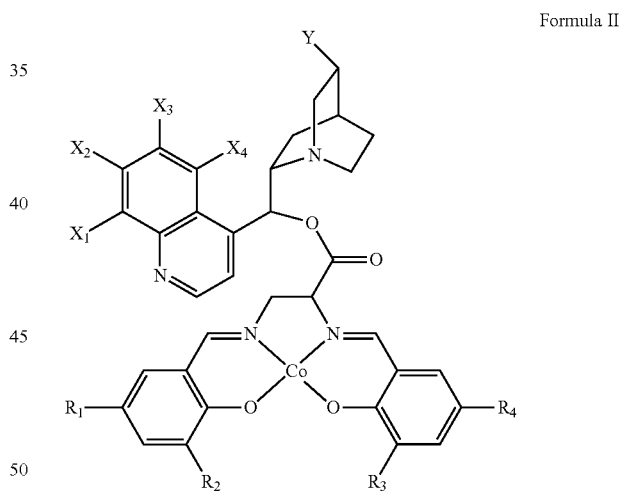

Formula II wherein one of X1 through X4 is alkoxy, alkyl, or a linker and the remaining three are hydrogen; Y is alkyl, alkenyl, or alkynyl; and R1 through R4 are alkyl (C3-10) or silyl; or
wherein one of X1 through X4 is O-methyl or vinyl and the remaining three are hydrogen; Y is vinyl; and R1 through R4 are isopropyl or t-butyl; or
wherein X1, X2 and X4 are hydrogen; X3 is O-methyl; Y is vinyl; R1 through R4 are each t-butyl; or
wherein one of X1 through X4 are alkyl and the remaining three are hydrogen; Y is hydrogen, alkoxy, alkyl, or a linker; Y is alkyl, alkenyl, or alkynyl; and R1 through R4 are alkyl (C3-10) or silyl; or
wherein one of X1, X2, and X4 is alkoxy and the other two are hydrogen; X3 is hydrogen; Y is alkyl (C3-10); and R1 through R4 are alkyl (C3-10) or silyl; or wherein X1, X2 and X4 are each hydrogen; X3 is vinyl; Y is vinyl; and R1 through R4 are isopropyl or t-butyl.

Particularly provided are methods to make oxidized COII compounds herein, wherein the oxidant is selected from the group consisting of: AgSbF6 and AgBF4. Also provided are products made from those methods/processes.

Also provided are methods to make a compound of the Formula II

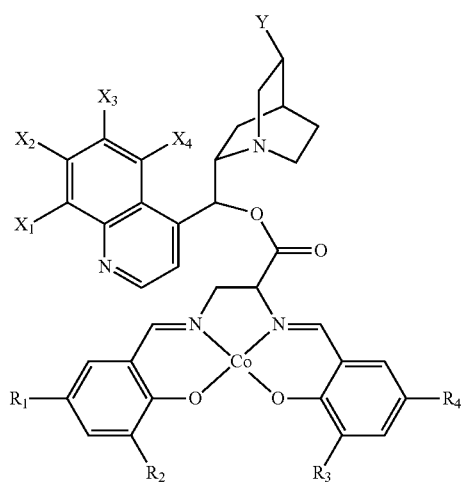

Formula II wherein one of X1 through X4 is alkoxy, alkyl, or a linker and the remaining three are hydrogen; Y is alkyl, alkenyl, or alkynyl; and R1 through R4 are alkyl (C3-10) or silyl; or wherein one of X1 through X4 is O-methyl or vinyl and the remaining three are hydrogen; Y is vinyl; and R1 through R4 are isopropyl or t-butyl; or wherein X1, X2 and X4 are hydrogen; X3 is O-methyl; Y is vinyl; R1 through R4 are each t-butyl; or wherein one of X1 through X4 are alkyl and the remaining three are hydrogen; Y is hydrogen, alkoxy, alkyl, or a linker; Y is alkyl, alkenyl, or alkynyl; and R1 through R4 are alkyl (C3-10) or silyl; or wherein one of X1, X2, and X4 is alkoxy and the other two are hydrogen; X3 is hydrogen; Y is alkyl (C3-10); and R1 through R4 are alkyl (C3-10) or silyl; or wherein X1, X2 and X4 are each hydrogen; X3 is vinyl; Y is vinyl; and R1 through R4 are isopropyl or t-butyl, comprising:

synthesizing a salen ligand from diamine and quinine, complexing the salen ligand from step a.) with cobalt.

Particularly provided are such methods which further comprise a step of oxidizing the cobalt to produce an oxidized Formula II. Particularly provided are such methods, wherein the oxidant is selected from the group consisting of: AgSbF6 and AgBF4. Also provided are products made from those methods/processes.

Also provided are methods to make compounds herein, comprising oxidizing a compound of Formula II

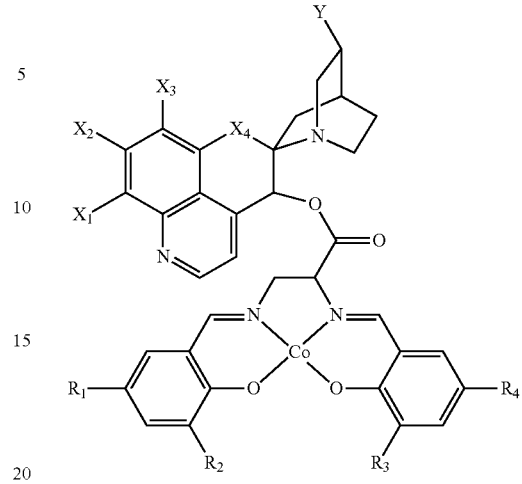

Formula II wherein one of X1 through X4 is alkoxy, alkyl, or a linker and the remaining three are hydrogen; Y is alkyl, alkenyl, or alkynyl; and R1 through R4 are independently alkyl (C3-10) or silyl.

Particularly provided are those methods wherein the oxidant is selected from the group consisting of: AgSbF6 and AgBF4.

Also provided are those methods wherein the oxidant is AgSbF6.

Products made according to the present processes/methods are also provided.

Also provided are methods to use the present compositions.

Provided are methods to make a composition comprising at least one β-lactone constituent, comprising co-mingling a compound of any of compound or compositions herein so as to produce a β-lactone-forming reaction between at least one ketene and at least one aldehyde in a container.

Particularly provided are those methods wherein the compound is introduced to the container first, the aldehyde second, and the ketene third, amongst those three.

Particularly provided are those methods wherein the container is selected from a group consisting of: commercial batch processor, commercial continuous process line, and laboratory vessel.

Particularly provided are those methods wherein the ketene is a pure ketene.

Particularly provided are those methods wherein the ketene is made from acetone via pyrolysis.

Particularly provided are those methods wherein the reaction is less than 2 hours, less than 1 hour, or less than 30 minutes.

Particularly provided are those methods wherein the reaction is accomplished at a temperature of from about room temperature to less than about 0° C.

Particularly provided are those methods which are accomplished at less than −70° C., or less than around −78° C.

Particularly provided are those methods wherein the aldehyde is an aromatic aldehyde.

Particularly provided are those methods wherein the aldehyde is an aliphatic aldehyde.

Particularly provided are those methods as represented by scheme 4:

Scheme 4

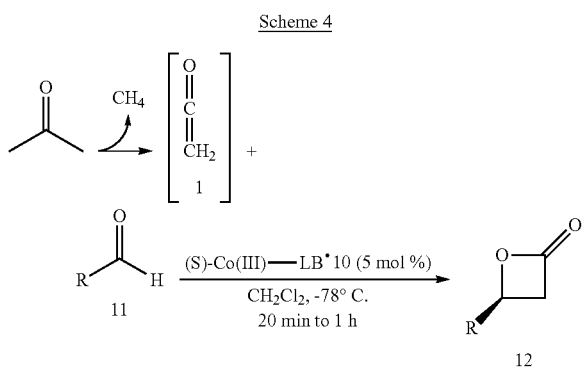

wherein R in the aldehyde (11) is selected from the group consisting of: 3-FC6H4−; 3-ClC6H4−; 2-ClC6H4−; 2-FC6H4; PhCH2−; PhCH2CH2−; n-C6H13−; or n-C11H23-.

Provided are any of these methods wherein the composition comprising β-lactone constituent is produced in enantiomeric excess of at least about 70%, at least about 80%, at least about 90%, at least about 95%, at least about 98%.

Provided are any of these methods wherein the compound is present at from about 0.01 mole percent to about 10 mole percent, present at from about 0.1 mole percent to about 5 mole percent, present at from about 0.05 mole percent to about 1 mole percent, or present at about 0.5 mole percent.

Provided are any of these methods with a yield of at least about 70%, at least about 80%; at least about 85%, at least about 90%; or at least about 95%

Also provided are methods to make enantiomerically-selected pharmaceutical compounds comprising catalyzing ketene and aldehyde to produce at least one β-lactone intermediate using at least one compound of any of claims 1 through 23, 36 or 39 as the catalyst.

Particularly provided are those methods wherein the enantiomerically-selected pharmaceutical is produced via a β-lactone intermediate with enantiomeric excess of at least about 90%, at least about 95%, at least about 98%.

Products made according to the processes/methods are also provided.

DEFINITIONS

The term "lactone" refers a cyclic ester. The term beta-lactone (i.e., "β.-lactone") is intended to indicate that the ring in the lactone is a four member ring.

The term "linker" refers to any chemical group which would allow binding of the catalyst to another chemical entity or solid support. This term includes any reactive group, but especially any reactive group. In particular, acids which can form an ester with an OH group on a solid support are within this definition, as are halogens. The choice of linker depends on the groups on the solid support or chemical. If the solid support contains acids, for example, then an alcohol or halogen would be useful. Therefore, "linker" is defined broadly, and includes acids, alcohols, thiols, halogens, amines, aldehydes, peroxides, etc. Covalent linkers are included in this definition.

The term "aldehyde" refers to an organic compound which incorporates a carbonyl functional group, and where at least one of two remaining bonds is occupied by hydrogen.

The term "alkyl" includes substituted alkyl and refers, respectively, to substituted and unsubstituted C1-10 straight chain saturated aliphatic hydrocarbon groups, substituted and unsubstituted C2-10 straight chain unsaturated aliphatic hydrocarbon groups, substituted and unsubstituted C4-10 branched saturated aliphatic hydrocarbon groups, substituted and unsubstituted C4-10 branched unsaturated aliphatic hydrocarbon groups, substituted and unsubstituted C3-8 cyclic saturated aliphatic hydrocarbon groups, substituted and unsubstituted C5-8 cyclic unsaturated aliphatic hydrocarbon groups having the specified number of carbon atoms. The definition of "alkyl" includes, but is not limited to, any of the following: methyl (Me), ethyl (Et), propyl (Pr), butyl (Bu), pentyl, hexyl, heptyl, octyl, nonyl, decyl, undecyl, ethenyl, propenyl, butenyl, penentyl, hexenyl, heptenyl, octenyl, nonenyl, decenyl, undecenyl, isopropyl (i-Pr), isobutyl (i-Bu), tert-butyl (t-Bu), sec-butyl (s-Bu), isopentyl, neopentyl, cyclopropyl, cyclobutyl, cyclopentyl, cyclohexyl, cycloheptyl, cyclooctyl, cyclopentenyl, cyclohexenyl, cycloheptenyl, cyclooctenyl, methylcyclopropyl, ethylcyclohexenyl, butenylcyclopentyl, adamantyl, norbornyl and the like.

The term "effective amount" of a compound made according to the present methods refers a non-toxic but sufficient amount of the compound that provides a desired effect. This amount may vary from subject to subject, depending on the species, age, and physical condition of the subject, the severity of the disease that is being treated, the particular compound used, its mode of administration, and the like. Therefore, it is difficult to generalize an exact "effective amount," yet, a suitable effective amount may be determined by one of ordinary skill in the art using commonly known techniques and methodologies.

The term "pharmaceutically acceptable" refers to a compound, additive or composition that is not biologically or otherwise undesirable. For example, the additive or composition may be administered to a subject along with a compound of the invention without causing any undesirable biological effects or interacting in an undesirable manner with any of the other components of the pharmaceutical composition in which it is contained.

The term "pharmaceutically acceptable salts" includes hydrochloric salt, hydrobromic salt, hydroiodic salt, hydrofluoric salt, sulfuric salt, citric salt, maleic salt, acetic salt, lactic salt, nicotinic salt, succinic salt, oxalic salt, phosphoric salt, malonic salt, salicylic salt, phenylacetic salt, stearic salt, pyridine salt, ammonium salt, piperazine salt, diethylamine salt, nicotinamide salt, formic salt, urea salt, sodium salt, potassium salt, calcium salt, magnesium salt, zinc salt, lithium salt, cinnamic salt, methylamino salt, methanesulfonic salt, picric salt, tartaric salt, triethylamino salt, dimethylamino salt, tris(hydroxymethyl)-aminomethane salt and the like. Additional pharmaceutically acceptable salts are known to those of skill in the art.

BRIEF DESCRIPTION OF THE DRAWINGS

Part I

FIG. 1—Scheme 1—Prior Art is a schematic illustration of the catalytic cycle of the Wynberg reaction.

FIG. 2—Scheme 2 is a schematic illustration of an enolizable 3-benzyloxypropanal selected as a substrate for initial optimization studies.

FIG. 3A—Prior Art is a schematic illustration of a salen-Co(II) based LA*-LB* bi-functional catalyst (6), as developed by the inventor herein.[7]

FIG. 3B—Scheme 3 is a schematic illustration of the oxidation of (S)—Co(II)-LB* (catalyst 9) to (S)—Co(III)-LB* (catalyst 10) using $AgSbF_6$ for improved catalytic activity.

FIG. 4—Scheme 4 is a schematic illustration of Co(III)-based LA*-LB* bi-functional catalyst applicable to both aromatic and enolizable aliphatic aldehydes in the LA*-LB* catalyzed [2+2] reaction.

FIG. 5—Scheme 5 is a schematic illustration of an intramolecular asymmetric bi-functional catalysis.

Part II

FIG. 6—Scheme 6 is a schematic illustration of synthesis of optically pure hydroxamate aldols using aldehydes, acetone, and O-benzylhydroxyamine as starting materials, as generally shown in Table 4.

FIG. 7—Scheme 7 is a schematic illustration of a catalytic and enantioselective synthesis of β-lactones from aldehydes and ketene precursor acetone.

FIG. 8—Scheme 8 is a schematic illustration showing Equation 1, where the optical purity of the β-lactones is translated into that of the resulting hydroxamate aldols.

Part III

Figure 9:
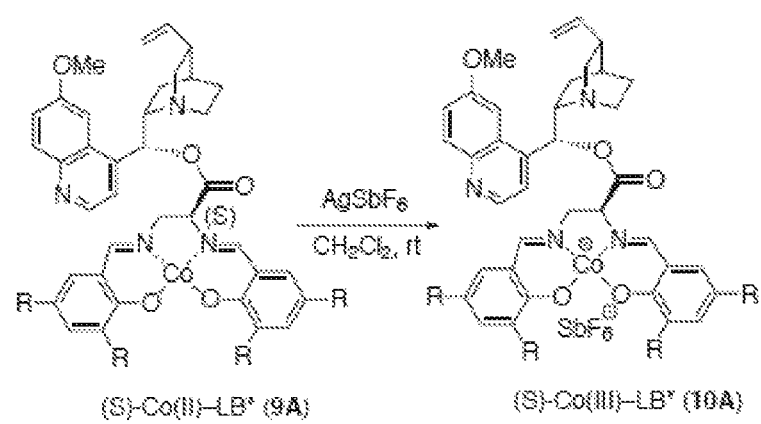

FIG. 9—Scheme 9 is a schematic illustration of oxidation of (S)—Co(II)-LB* catalyst to (S)—Co(III)-LB*.

FIGS. 10 and 10A depict illustrated examples of bifunctional catalysts claimed herein; FIGS. 10A1 and 10A2 depict illustrated examples of stereoisomers of bifunctional catalysts herein.

Figure 11:
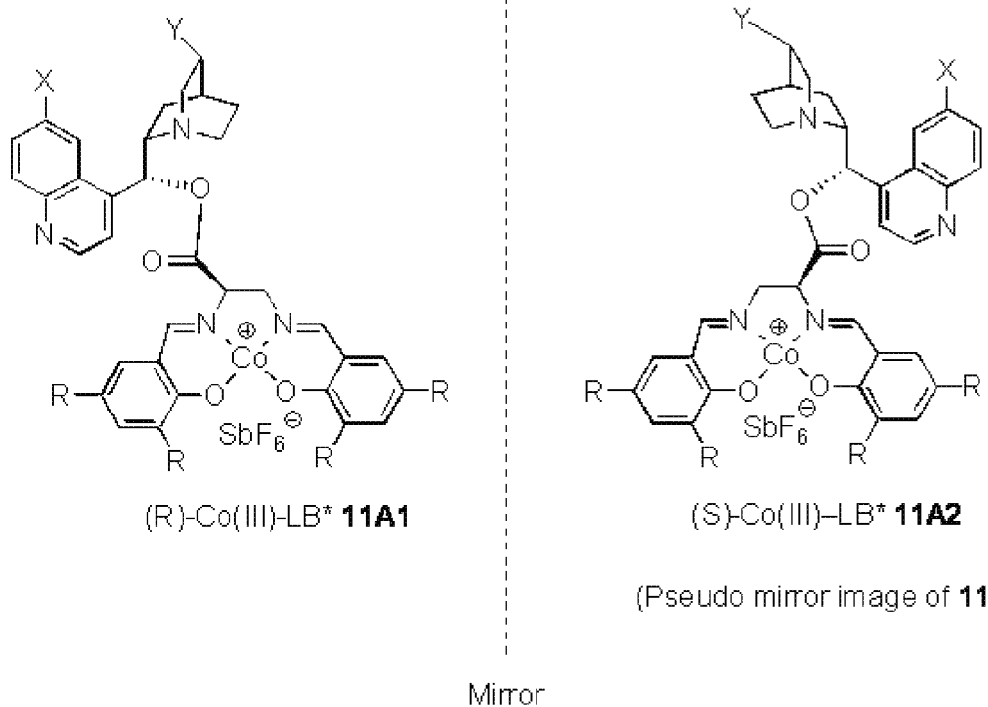

FIGS. 11A1 and 11A2 depict illustrated examples of stereoisomers of bifunctional catalysts herein.

FIGS. 12A1 and 12A2 depict illustrated examples of stereoisomers of bifunctional catalysts herein.

Figure 13:
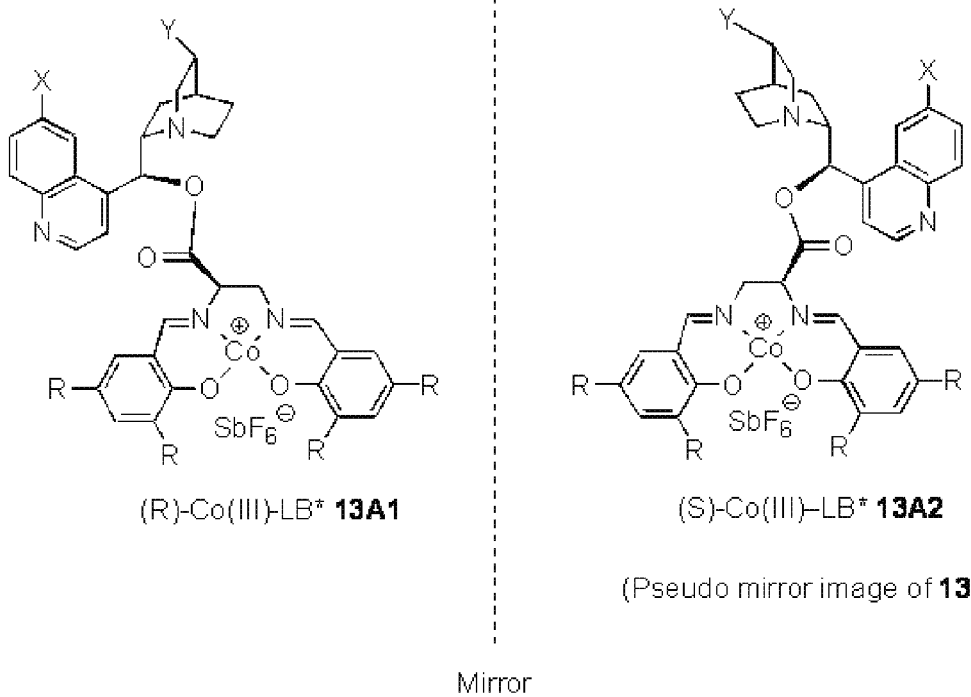

FIGS. 13A1 and 13A2 depict illustrated examples of stereoisomers of bifunctional catalysts herein.

DETAILED DESCRIPTION OF THE INVENTION

Throughout this disclosure, various publications, patents and published patent specifications are referenced by an identifying citation. The disclosures of these publications, patents and published patent specifications are hereby incorporated by reference into the present disclosure to more fully describe the state of the art to which this invention pertains.

Part I

In certain embodiments, one or more R moieties shown in (10A) can be substituted by: H, branched or unbranched, alkyl or aryl groups. Also, in certain embodiments, R represents independently for each occurrence H, alkyl or aryl group.

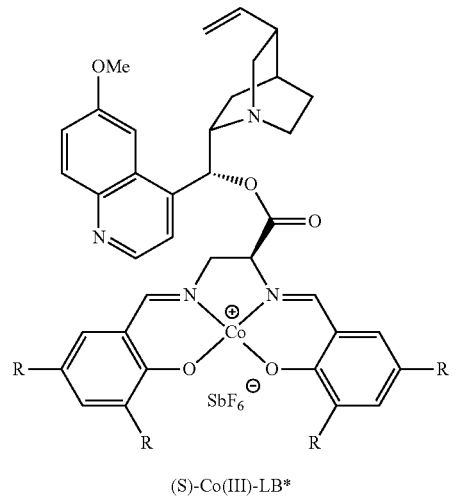

(10A)

(S)-Co(III)-LB*

For example, in one non-limiting embodiment, R represents independently for each occurrence alkyl. In another non-limiting embodiment, one or more R moieties represent t-butyl. In a particular aspect, there is provided herein a catalyst compound represented by the bi-functional catalyst having the structure (10) shown herein.

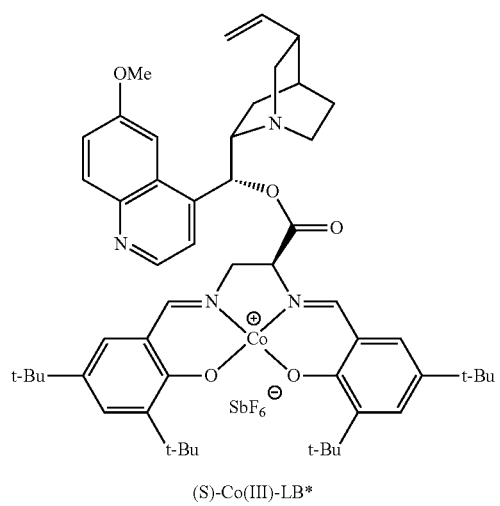

(10)

(S)-Co(III)-LB*

In certain embodiments, the bi-functional catalyst is used to make β-lactone compounds having the structure (12) shown herein. In certain embodiments, the β-lactone compounds are present in an enantiomeric excess (ee) greater than or equal to about 70%, about 80%; about 90%; about 95%; or about 99%.

In another aspect, there is provided herein the use of the compounds (10) and (10A) in a catalytic, enantioselective [2+2] cycloaddition reaction between an aldehyde and unsubstituted ketene.

In one method, substantially pure ketene (1) is added to an aldehyde (11) in the presence of the bi-functional catalyst (10).

In another aspect, there is provided herein a method of producing a β-hydroxy ester comprising using at least one β-lactone (12) produced as described herein.

In another aspect, there is provided herein a method of making a desired enantiomer of a compound of β-lactone (12), or a pharmaceutically acceptable complex, salt, solvate or hydrate thereof. The method includes: reacting a compound of structure (11) with a ketene (1) in the presence of a bi-functional catalyst to yield the β-lactone (12); and, optionally converting the β-lactone (12) into a pharmaceutically acceptable complex, salt, solvate or hydrate.

In another aspect, there is provided herein a process enantioselectively producing a β-lactone compound, the method comprising: enantioselectively converting a ketene into an ammonium enolate using a Lewis acid-Lewis base bi-functional catalyst, and delivering the ammonium enolate into an aldehyde in the presence of the bi-functional catalyst under conditions sufficient to produce β-lactone compound.

In certain embodiments, the enantioselective conversion of the aldehyde produces the β-lactone compound in an enantiomeric excess (ee) of at least about 90%.

In certain embodiments, lactonization of the bi-functional catalyst produces the β-lactone compound and regenerates the bi-functional catalyst. In certain embodiments, the bi-functional catalyst is a compound of the structure (10).

Part II

In another aspect, there is provided herein a method for making a substantially optically pure hydroxamate aldol.

In another aspect, there is provided herein use of one or more β-lactone compounds as a substantially optically pure chiral compound for forming at least one of: β-lactams, and β-amino acids.

Part III

Compounds

The present invention provides oxidized CO(II) catalysts, namely the bifunctional catalysts shown in FIG. 1.

Ideally, the compounds are stabilized, such as being present with at least counterion, or provided in a medium which ameliorates deterioration of the compound. In addition, modifications to the compound such that the compound may be re-used or recycled are useful. For instance, the compounds may be modified so as to be affixed to beads, resins, silica, alumina, zeolites, porous membranes, nanoparticles or other solid support, for ease of purification/removal after use.

Compositions of Matter

In that regard, the present invention also provides compositions comprising the present compounds. In particular, those compositions useful to stabilize, purify, use or analyze the compounds, compositions, reaction products, or reaction parameters are included in the present invention. Moreover, since the CO(II) precursor is useful in producing the present compounds, compositions comprising CO(II) precursor and CO(III) and the bifunctional catalysts of Formula I are also provided.

Methods of Making

Synthesis of Ligand To a solution of the (S)-Boc-protected ester (2.0 g, 3.28 mmol) in $CH_2Cl_2$ (10 mL) at 0° C., was added TFA (10 mL). The solution was stirred at 0° C. for 1 hour and the volatiles were evaporated to give the TFA salt as an oil, which was transferred to a separatory funnel and participated between methylene chloride (ca. 300 mL) and saturated sodium bicarbonate. The residual TFA was neutralized with solid sodium bicarbonate to pH ~7-8, and layers were separated. The aqueous phase was extracted with methylene chloride. The combined organic phases were dried ($Na_2SO_4$), filtered, and concentrated to give 1.24 g of diamine (92%) as a white foam.

To a solution of the above diamine (1.24 g, 3.02 mmol) in isopropanol (10 mL) at room temperature, was added a solution of 3,5-di-t-butyl-2-hydroxybenzaldehyde (1.27 g, 5.43 mmol) in methylene chloride (10 mL) to give an orange solution, to which 4 Å molecular sieves was added. The reaction was stirred at room temperature for 10 hours. The molecular sieves were filtered off and rinsed with methylene chloride. The filtrate was concentrated to give 2.34 g (92%) of the salen ligand as a yellow foam.

Synthesis of (S)—Co(II)-LB* complex: The salen ligand (2.0 g, 2.37 mmol) was dissolved in THF (100 mL) at room temperature. The resulting orange solution was degassed at room temperature for 0.5 h, followed by the addition of anhydrous $CoCl_2$ (0.283 g, 2.18 mmol). The blue $CoCl_2$ dissolved slowly to give a deep red solution, which was refluxed in an oil bath for 2 hour. THF was distilled off (ca 80 mL) to give a concentrated solution, to which degassed pentane (ca. 200 mL) was added to the warm residue, to precipitate the Co(II)-salen complex as a HCl salt. The mixture was cooled to room temperature. The solid was separated, dried under vacuum (ca. 0.1 torr) to give 1.45 g (68%) of the desired (S)—Co(II)-salen complex as a light brown powder. High resolution mass spectrometry calculated for $C_{53}H_{70}N_4O_5Co$ $[M+H]^+$: 901.4678. found: 901.4529.

Methods of Using

Examples of the disorders, diseases, and pathologies that can be treated using the compounds made according to the present invention include, but are not limited to, hyperproliferative diseases such as cancer (including breast cancer, prostate cancer, ovarian cancer, colon cancer, non-small cell lung cancer, lung cancer, brain cancer, esophageal cancer, or liver cancer, and various types of leukemia), atherosclerosis, restenosis, inflammation, auto-immune diseases, diseases associated with angiogenesis including diabetic retinopathy, macular degeneration, arthritis, burns, and infectious diseases and disorders such as urinary tract infection, bladder infection, skin infections (e.g., pustulant skin sores), Yersinia infection, pneumonic plague, tuberculosis, and lung lesions similar to tuberculosis.

For example, the following patent documents are incorporated by reference, with each presenting pharmaceuticals for which the present invention provides an improvement in synthesis. The synthesis of these, and any other pharmaceutical engineered to include a beta lactone intermediate, can be improved in enantiomeric selectivity and yield: U.S. Pat. No. 6,933,393; U.S. Pat. No. 5,273,995; U.S. Pat. No. 4,598,089; U.S. Pat. No. 7,144,915; US Publication 2003/0212279; U.S. Pat. No. 6,646,133; US Publication 2006/0211761; US 2007/0166360; US Publication 2002/0028833; US Publication 2005/0239869; US Publication 2006/0252816; U.S. Pat. No. 5,385,929; U.S. Pat. No. 6,605,729; US Publication 2006/0241169; U.S. Pat. No. 5,958,950; U.S. Pat. No. 6,184,235; U.S. Pat. No. 6,011,052; U.S. Pat. No. 6,177,121; U.S. Pat. No. 6,605,636; U.S. Pat. No. 6,476,235; US Publication 2006/0229363; US Publication 2005/0261359; US Publication 2006/0142592; U.S. Pat. No. 7,342,120; US Publication 2001/0018427; U.S. Pat. No. 7,161,012; US Publication 2003/0162827; US Publication 2005/0038007; US Publication 2006/0128971; US Publication 2007/0032662; US Publication 2005/0271717; US Publication 2004/0220254; U.S. Pat. No. 7,361,772; U.S. Pat. No. 6,087,511; and US Publication 2006/0205804.

Pharmaceutically acceptable salts of the compounds made according to the methods of the present invention may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

The above-described pharmaceutical products can be formulated as pharmaceutical compositions and administered to a mammalian host, such as a human patient in a variety of forms adapted to the chosen route of administration, i.e., orally or parenterally, by intravenous, intramuscular, topical or subcutaneous routes.

Thus, the pharmaceutical products may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The active compound may also be administered intravenously or intraperitoneally by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, the pharmaceutical products may be applied in pure form, i.e., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Useful dosages can be determined by comparing their in vitro activity, and in vivo activity in animal models. Methods for the extrapolation of effective dosages in mice, and other animals, to humans are known to those having ordinary skill in the art.

EXAMPLES

The present invention is further defined in the following Examples, in which all parts and percentages are by weight and degrees are Celsius, unless otherwise stated. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions. All publications, including patents and non-patent literature, referred to in this specification are expressly incorporated by reference herein.

Part I

Comparative Example 1

The inventor herein initially attempted to expand the substrate scope of the [2+2] cycloaddition reaction catalyzed by the bi-functional catalyst 6 (shown in FIG. 3A—Prior Art).

Enolizable 3-benzyloxypropanal (7) was chosen as the substrate for initial optimization studies (FIG. 2-Scheme 2). However, the Co(II)-based LA*-LB* bi-functional catalyst 6 proved less active for aldehyde 7, in spite of many attempts. For example, when ketene 1 was generated slowly in situ from acetyl chloride and Hünig's base[10], the catalyst 6 (10 mol %) gave only 6% conversion of the reaction after 12 h at −78° C. (entry #1, Table 1 below).

The (S)—Co(II)-LB* catalyst 9 (LB*=quinine) was subsequently synthesized from the corresponding ligand, which was derived from the (S)-diaminopropionic acid linker, and anhydrous $CoCl_2$, as a light-brown powder, using a modified procedure. However, the (S)—Co(II)-LB* bi-functional catalyst 9 also did not show an improvement in catalytic activity for aldehyde 7. Employing the (S)—Co(II)-LB* catalyst 9 (10 mol %) produced little conversion of the aldehyde (entry #2, Table 1 below). In the low conversion reactions, competing side reactions dominated to produce the undesired ketene dimers.

Example 1

Development of Active Bi-Functional Catalyst

The metal in catalyst 9 was oxidized from Co(II) to Co(III). It has now been discovered that the Co(III)-based bi-functional catalyst 10 was more active since the Co(III)-salen complex displays enhanced Lewis acidity over its Co(II) analog.

After oxidizing the Co(II) in catalyst 9 to Co(III) using $AgSbF_6$, an improved catalytic activity (FIG. 3B—Scheme 3B) was observed. The Co(III)-based bi-functional catalyst 10 (5 mol %) promoted the [2+2] reaction to produce the desired β-lactone 8 in 45-65% yields and >99% ee (entries #3 and #4, Table 1 below), when ketene was generated in situ by slowly adding (via a syringe pump) acetyl chloride to the reaction containing Hünig's base.

In certain non-limiting embodiments, the acetyl chloride methylene chloride solution can be added over a period of time (e.g., six hours) in order to produce the desired β-lactone in good yields. In contrast, regular drop-wise addition of acetyl chloride to the reaction gave very little conversions. While not wishing to be bound by theory, the inventor herein now believes that the isolated ketene dimer by-product is produced from the reaction between the unreactive ketene and the ammonium enolate species.

In addition to the variable isolated yields (e.g., entries #3 and #4, Table 1 below), employing the acetyl chloride/Hünig's base protocol for generating the ketene in situ, there were additional limitations in the LA*-LB* catalyzed enantioselective cyclization reaction. First, ketene formation from the acetyl chloride can be the rate-determining step, which would diminish the catalytic efficacy of the LA*-LB* bi-functional catalyst. Second, the chloride anion formed during the reaction can coordinate to the Co(III), sequestering the cationic Co(III) catalytic species into a stable hexacoordinate complex.

In order to avoid the pre-equilibrium ketene-forming step that limits the overall reaction rate, the inventor herein determined that Wynberg's protocol, which utilizes pure ketene, can be used. That is, the inventor herein has now discovered that by employing pure ketene in the reaction, the competitive side reaction between the ammonium enolate and the acetyl chloride is eliminated. Thus, without generating the chloride anion during the reaction, its coordination to the Co(III) is avoided, thereby preventing the conversion of the LA* from the cationic Co(III) into a less Lewis acidic species.

In addition, pure ketene can be generated conveniently from inexpensive acetone via pyrolysis, through a modified ketene lamp.[13] After the ketene gas was bubbled into the reaction at −78° C., the Co(III)-derived bi-functional catalyst 10 (5 mol %) promoted the reaction rapidly. The reaction was complete within eight minutes, affording the β-lactone 8 in 82% yield and >99% ee (entry #5, Table 1 below). The R-configuration of the β-lactone 8 was established experimentally.

In contrast, the (S)—Co(II)-based bi-functional catalyst 9 proved to be inactive for the same reaction, under similar reaction conditions (entry #6, Table 1 below). Taken together, these examples show that enhanced Lewis acidity is desirable for a very active LA*-LB* bi-functional catalyst, which is necessary for the unprecedented rate acceleration. In addition, it is desirable to employ pure ketene, rather than the acetyl chloride/Hünig's base as the ketene source in the reaction, in order to attain the desired rate acceleration.

TABLE 1

Initial Reaction Optimization Studies

| Entry[a] | LA*-LB* Catalyst (mol %) | Reaction time (h) | Yield (%)[b] | ee (8)[c] |
|---|---|---|---|---|
| #1 | 6 (10) | 12 | 6 | — |
| #2 | 9 (10) | 12 | 5-6 | — |
| #3 | 10 (5) | 12 | 45 | >99% |
| #4 | 10 (5) | 12 | 65 | >99% |
| #5 | 10 (5) | 8 min | 82 | >99% |
| #6 | 9 (5) | 2 | — | — |

[a]Reaction concentration [7] = 0.1M; ketene was generated either from acetyl chloride/Hünig's base in situ (entries #1-#4) or via pyrolysis of acetone (entries #5 and #6). For entry 3, acetyl chloride was added slowly (3 h) to the reaction and the reaction was stirred at −78° C. for 12 h. For entry #5, ketene gas was bubbled into the reaction. See Example 2 below for experimental details.
[b]Isolated yields (entries #3-#5), except for entries #1 and #2, where conversion % was estimated by crude $^1H$ NMR.
[c]The ee was determined by chiral HPLC.

Example 2

Aromatic and Enolizable Aliphatic Aldehydes

The Co(III)-based LA*-LB* bi-functional catalyst 10 was applicable to both aromatic and enolizable aliphatic aldehydes (see FIG. 4-Scheme 4, and Table 2 below). For example, the LA*-LB* catalyzed [2+2] reaction was carried out in 0.1 M substrate concentrations. The catalyst (5 mol %) promotes the reaction rapidly at −78° C. after ketene (~2-3 equiv) was bubbled into the methylene chloride solution. Halogenated aromatic aldehydes (entries #1-#4, Table 2 below) and phenylacetaldehyde (entry #5, Table 2 below) yielded complete reactions in about 20 minutes, furnishing the corresponding β-lactones 12 in excellent yields and >99% ee.

When other enolizable aliphatic aldehydes were employed, the reaction was complete within one hour and afforded the corresponding β-lactones 12 in excellent yields and >99% ee (entries #6-#8, Table 2 below). The absolute configurations of β-lactones 12 were established experimentally, and all were consistent with those predicted from empirical models.[9]

TABLE 2

Reaction Rate Acceleration Enabled by
Tethered Lewis Acid-Lewis Base Bi-functional Catalysis

| Entry[a] | R (11) | Time | Yield 12 (%)[b] | ee % (R/S)[c] |
|---|---|---|---|---|
| #1 | 3-FC$_6$H$_4$— | 20 min | 87 | >99 (S) |
| #2 | 3-ClC$_6$H$_4$— | 20 min | 97 | >99 (S) |
| #3 | 2-ClC$_6$H$_4$— | 20 min | 95 | >99 (S) |
| #4 | 2-FC$_6$H$_4$— | 20 min | 87 | >99 (S) |
| #5 | PhCH$_2$— | 20 min | 96 | >99 (R) |
| #6 | PhCH$_2$CH$_2$— | 1 h | 96 | >99 (R) |
| #7 | n-C$_6$H$_{13}$— | 1 h | 74 | >99 (R) |
| 8 | n-C$_{11}$H$_{23}$— | 1 h | 71 | >99 (R) |

[a]All reactions were carried out in 1 mmol scale, [11] = 0.1M, ketene was generated by pyrolysis of acetone.
[b]Isolated yield.
[c]The ee was determined by chiral HPLC and the R/S-configuration of the β-lactones 12 were established experimentally.

Example 3

Open Transition-State Intermediate

An open transition-state model intermediate 13 can account for the intramolecular bi-functional catalytic cycle, as shown in FIG. 5—Scheme 5. The LB* moiety of catalyst 10 converts the ketene into an ammonium enolate, and delivers it to the Co(III)-activated aldehyde in an intramolecular manner. The resulting Co(III)-aldolate 14 lactonizes to furnish β-lactone 12 and regenerate catalyst 10. The rapid catalyst turnover is indicative of a weak aldolate-Co(III) interaction, thus ensuring the catalytic cycle. Because the LA* coordination sites in catalyst 10 are openly accessible for substrates, the excellent ee of the reaction is consistent with the LB*-dependent asymmetric induction process described herein.

Example 4

LA*-LB* Catalyzed Asymmetric [2+2] Cycloaddition Reaction (R)-4-(2-Benzyloxyethyl)oxetan-2-one (8)

To a solution of catalyst 9.2HCl (49 mg, 0.05 mmol) in methylene chloride (2.0 mL) at room temperature was added AgSbF$_6$ (52 mg, 0.15 mmol). The resulting dark-brown mixture was stirred at room temperature for 1.5 hours, followed by the addition of methylene chloride (8.0 mL), diisopropylethylamine (0.10 mL, 0.61 mmol), and aldehyde 7 (164 mg, 1.0 mmol). The solution was cooled to −78° C. and ketene gas (~2-3 equiv) generated via pyrolysis of acetone was bubbled into the reaction mixture for 8 minutes to give a complete reaction, as indicated by TLC. The reaction was quenched with saturated NaHCO$_3$ at −78° C., warmed up to room temperature, and extracted with methylene chloride. The combined organic phases were washed with brine, dried (Na$_2$SO$_4$), filtered, concentrated and separated by flash column chromatography on silica gel (hexanes-EtOAc, 16:1→8:1→4:1) to give β-lactone 8. Table 3 below contains the HPLC conditions used to analyze the samples listed in Table 2.

Yield: 168 mg (82%); oil. $^1$H NMR (400 MHz, CDCl$_3$): δ=7.37-7.27 (m, 5H), 4.68 (m, 1H), 4.50 (s, 2H), 3.62 (m, 2H), 3.53 (dd, J=16.4, 5.6 Hz, 1H), 3.17 (dd, J=16.4, 4.4 Hz, 1H), 2.11 (m. 2H). $^{13}$C NMR (100 MHz, CDCl$_3$): δ=168.2, 137.8, 128.4, 127.8, 127.6, 73.0, 69.1, 65.7, 43.1, 34.7. IR (neat): 1825.4, 1191.1 cm$^{-1}$.

Chiral HPLC analysis of β-lactone 8 gave a single peak at 15.0 minutes (>99% ee). Under the same HPLC conditions, a racemic sample gave two well-resolved peaks. HPLC conditions: HPLC column=CHIRALCEL OD-H (0.46×25 cm); i-PrOH-hexanes, 15:85 (v/v); flow rate=1.0 mL/min; UV detection: 210 nm.

TABLE 3

Summary of HPLC Conditions Corresponding to the Entries in Table 2

| Entry | i-PrOH-hexanes mobile phase (v/v) and flow rate (mL/min) | T$_R$ (min) | UV detection λ (nm) |
|---|---|---|---|
| #1[a] | 10:90 (1.0) | 6.6 | 260 |
| #2[a] | 10:90 (1.0) | 7.7 | 210 |
| #3[a] | 20:80 (0.5) | 9.7 | 220 |
| #4[a] | 20:80 (0.5) | 8.9 | 260 |
| #5[b] | 10:90 (1.0) | 13.3 | 210 |
| #6[b] | 10:90 (1.0) | 16.3 | 210 |
| #7[c] | 4:96 (1.0) | 8.0 | 210 |
| #8[d] | 3:97 (1.0) | 12.4 | 210 |

[a]HPLC analysis was carried out on their corresponding β-hydroxy methyl esters.
[b]HPLC analysis was carried out on the β-lactones.
[c]HPLC analysis was carried out on the (S)—O-methylmandelate of its β-hydroxy methyl ester.
[d]HPLC analysis was carried out on the (R)—O-methylmandelate of its β-hydroxy methyl ester.

Part II

Example 5

Synthesis of Optically Pure Hydroxamate Aldols

Synthesis of optically pure hydroxamate aldols using readily available aldehydes, acetone, and O-benzylhydroxyamine as the starting materials can be performed as shown in FIG. 6—Scheme 6. The highly efficient rate acceleration enabled via the intramolecular bi-functional catalysis, coupled with the uniformly highly desirable enantioselectivity (>99% ee) observed in the product, provides an improved process for derivatizing β-lactones to produce other valuable chiral synthons.

Non-limiting examples, such as the formal synthesis of optically pure hydroxamate aldols from aldehydes, are shown in FIG. 7-Scheme 7.

Example 6

Opening the β-lactones with O-alkylhydroxylamines Furnishes Hydroxamate Aldols

Since the hydroxylamine nucleophile attacks the carbonyl group (FIG. 8), the optical purity of the β-lactones is translated into that of the resulting hydroxamate aldols. Single enantiomeric hydroxamate aldols are obtained in high isolated yields (Table 4).

TABLE 4

Optically Pure Hydroxamate Aldols from Aldehydes

| Entry | R-(RCHO Aldehydes) | Yield (% ee) | Hydroxamate Aldols |
|---|---|---|---|
| #1 | BnOCH$_2$CH$_2$— | 79% (>99) | BnO–CH$_2$CH$_2$–CH(OH)–CH$_2$–C(O)–NHOBn |
| #2 | BnOCH$_2$— | 86% (>99) | BnO–CH$_2$–CH(OH)–CH$_2$–C(O)–NHOBn |
| #3 | CH$_3$(CH$_2$)$_4$CH$_2$— | 82% (>99) | CH$_3$(CH$_2$)$_4$CH$_2$–CH(OH)–CH$_2$–C(O)–NHOBn |
| #4 | CH$_3$(CH$_2$)$_9$CH$_2$— | 73% (>99) | CH$_3$(CH$_2$)$_9$CH$_2$–CH(OH)–CH$_2$–C(O)–NHOBn |
| #5 | PhCH$_2$CH$_2$— | 81% (>99) | Ph–CH$_2$CH$_2$–CH(OH)–CH$_2$–C(O)–NHOBn |
| #6 | PhCH$_2$— | 97% (>99) | Ph–CH$_2$–CH(OH)–CH$_2$–C(O)–NHOBn |
| #7 | 2-Chlorophenyl- | 83% (>99) | (2-Cl-C$_6$H$_4$)–CH(OH)–CH$_2$–C(O)–NHOBn |
| #8 | 2-Fluorophenyl- | 91% (>99) | (2-F-C$_6$H$_4$)–CH(OH)–CH$_2$–C(O)–NHOBn |
| #9 | 3-Chlorophenyl- | 73% (>99) | (3-Cl-C$_6$H$_4$)–CH(OH)–CH$_2$–C(O)–NHOBn |
| #10 | 3-Fluorophenyl- | 74% (>99) | (3-F-C$_6$H$_4$)–CH(OH)–CH$_2$–C(O)–NHOBn |
| #11 | 4-Nitrophenyl- | 90% (>99) | (4-O$_2$N-C$_6$H$_4$)–CH(OH)–CH$_2$–C(O)–NHOBn |
| #12 | 4-Cyanophenyl- | 99% (>99) | (4-NC-C$_6$H$_4$)–CH(OH)–CH$_2$–C(O)–NHOBn |

Part III

Example 7

Improved Procedure for the Synthesis of Stereochemically Well-Defined Bifunctional Catalyst Synthesis of Ligand To a solution of the (S)-Boc-protected ester (2.0 g, 3.28 mmol) in CH$_2$Cl$_2$ (10 mL) at 0° C., was added TFA (10 mL). The solution was stirred at 0° C. for 1 hour and the volatiles were evaporated to give the TFA salt as an oil, which was transferred to a separatory funnel and participated between methylene chloride (ca. 300 mL) and saturated sodium bicarbonate. The residual TFA was neutralized with solid sodium bicarbonate to pH ~7-8, and layers were separated. The aqueous phase was extracted with methylene chloride. The combined organic phases were dried (Na$_2$SO$_4$), filtered, and concentrated to give 1.24 g of diamine (92%) as a white foam.

To a solution of the above diamine (1.24 g, 3.02 mmol) in isopropanol (10 mL) at room temperature, was added a solution of 3,5-di-t-butyl-2-hydroxybenzaldehyde (1.27 g, 5.43 mmol) in methylene chloride (10 mL) to give an orange solution, to which 4 Å molecular sieves was added. The reaction was stirred at room temperature for 10 hours. The molecular sieves were filtered off and rinsed with methylene chloride. The filtrate was concentrated to give 2.34 g (92%) of the salen ligand as a yellow foam.

Synthesis of (S)—Co(II)-LB* complex: The salen ligand (2.0 g, 2.37 mmol) was dissolved in THF (100 mL) at room temperature. The resulting orange solution was degassed at room temperature for 0.5 h, followed by the addition of anhydrous CoCl$_2$ (0.283 g, 2.18 mmol). The blue CoCl$_2$ dissolved slowly to give a deep red solution, which was refluxed in an oil bath for 2 hour. THF was distilled off (ca 80 mL) to give a concentrated solution, to which degassed pentane (ca. 200 mL) was added to the warm residue, to precipitate the Co(II)-salen complex as a HCl salt. The mixture was cooled to room temperature. The solid was separated, dried under vacuum (ca. 0.1 torr) to give 1.45 g (68%) of the desired (S)—Co(II)-salen complex as a light brown powder. High resolution mass spectrometry calculated for C$_{53}$H$_{70}$N$_4$O$_5$Co [M+H]$^+$: 901.4678. found: 901.4529.

While the invention has been described with reference to various and preferred embodiments, it should be understood by those skilled in the art that various changes may be made and equivalents may be substituted for elements thereof without departing from the essential scope of the invention. In addition, many modifications may be made to adapt a particular situation or material to the teachings of the invention without departing from the essential scope thereof.

Therefore, it is intended that the invention not be limited to the particular embodiment disclosed herein contemplated for carrying out this invention, but that the invention will include all embodiments falling within the scope of the claims.

REFERENCES

The publication and other material used herein to illuminate the invention or provide additional details respecting the practice of the invention, are incorporated by reference herein, and for convenience are provided in the following bibliography.

Citation of the any of the documents recited herein is not intended as an admission that any of the foregoing is pertinent prior art. All statements as to the date or representation as to the contents of these documents is based on the information available to the applicant and does not constitute any admission as to the correctness of the dates or contents of these documents.

1. For selected reviews on β-lactones and their synthetic applications, see: (a) Pommier, A.; Pons, J.-M. *Synthesis* 1993, 441. (b) Yang, H. W.; Roma, D. *Tetrahedron* 1999, 55, 6403. (c) Schneider, C. *Angew. Chem. Int. Ed.* 2002, 41, 744; *Angew. Chem.* 2002, 114, 771. (d) Wang, Y.; Tennyson, R. L.; Romo, D. *Heterocycles* 2004, 64, 605.
2. For selected reviews, see: (a) Tidwell, T. T. *Eur. J. Org. Chem.* 2006, 563. (b) Orr, R. K.; Colter, M. A. *Tetrahedron* 2003. 59, 3545. For examples of β-lactone formation from silylketene, see: (c) Evans, D. A.; Janey, J. M. *Org. Lett.* 2001, 3, 2125. (d) Forslund, R. E.; Cain, J.; Colyer, J.; Doyle, M. P. *Adv. Synth. Catal.* 2005, 347, 87.
3. (a) Wynberg, H.; Staring, E. G. J. *J. Am. Chem Soc.* 1982, 104, 166. (b) Wynberg. H.; Staring, E. G. J. *J. Org. Chem.* 1985, 50, 1977.
4. Cortez, G. S.; Tennyson, R. L.; Romo. D. *J. Am. Chem. Soc.* 2001, 123, 7945.
5. (a) Nelson, S. G.; Zhu. C.; Shen. X. *J. Am. Chem. Soc.* 2004, 126, 14. (b) Zhu, C.; Shen, X.; Nelson, S. G. *J. Am. Chem. Soc.* 2004, 126, 5352. (c) Calter, M. A.; Tretyak, O. A.; Flascheriem, C. *Org. Lett.* 2005, 7, 1809.
6. (a) Wilson, I E; Fu, G C. *Angew. Chem. Int. Ed.* 2004, 43, 6358; *Angew. Chem.* 2004, 116, 6518. (b) Gnanadesikan, V.; Corey, E. *J. Org. Lett.* 2006, 8, 4943. (c) Kull, T.; Peters, R. *Adv. Synth. Catal.* 2007, 349, 1647. (d) Kull, T.; Peters, R. *Angew. Chem. Int. Ed.* 2008, 47, 5461; *Angew. Chem.* 2008. 120, 5541. (e) He, L; Lv, H.; Zhang, Y.-R.; Ye, S. *J. Org. Chem.* 2008, 73, 8101.
7. Lin, Y.-M., Boucau, J.; Li, Z.; Casarotto, V.; Lin, J.; Nguyen. A. N.; Ehrmantraut, *J. Org. Lett.* 2007, 9, 567.
8. For selected reviews on tethered Lewis acid-Lewis base bifunctional catalysts, see: (a) Paull, D. H.; Abraham, C. J.; Scerba, M T.; Alden-Danforth, E.; Lectka, T. *Acc. Chem. Res.* 2008, 41, 655. (b) Kanai, M.; Kato, N.; Ichikawa, E: Shibasaki, M. *Synlett* 2005, 1491. For selected examples of tethered bifunctional catalysts, see: (c) Ito. Y.; Sawainura, M.; Hayashi, T. J. *Am. Chem. Soc.* 1986. 108, 6405. (d) Josephsohn, N. S.; Kuntz, K. W.; Snapper, M. L.; Hoveyda, A. H. *J. Am. Chem. Soc.* 2001, 123, 11594. (e) DiMauro, E. F.; Kozlowski, M. C. *Org. Lett.* 2001, 3, 3053. (f) Ichikawa, E.; Suzuki. M.; Yabu, K.; Albert, M.; Kanai, M.; Shibasaki, M. *J. Am. Chem. Soc.* 2004, 126, 11808. (g) France, S.; Shah, M. H.; Weatherwax, A.; Wack, H.; Roth, J. P.; Lectka. T. *J. Am. Chem. Soc.* 2005, 127, 1206. (h) Fennie, M. W.; Dimauro, E. F.; O'Brien, E. M.; Annamalai, V.; Kozlowski, M. C. *Tetrahedron* 2005, 61, 6249.
9. Lin, Y.-M.; Li, Z.; Boucau. J. *Tetrahedron Lett.* 2007, 48, 5275.
10. For examples of generating ketene from acyl halides and Hinig's base in situ, see ref 2a and 5.
11. (a) Tokunaga, M.; Larrow, J. F.; Kakiuchi. F.; Jacobsen, E. N. *Science* 1997, 277, 936. (b) Jacobsen, E. N. *Ace. Chem. Res.* 2000, 33, 421.
12. For an example of oxidizing a Co(I)-salen complex to the corresponding Co(III)-salen complex using $AgSbF_5$ see: Hutson, G. E.; Dave, A. H.; Rawal, V. H. *Org. Lett.* 2007, 9, 3869.
13. Williams, J. W.; Hurd, C. D. *J. Org. Chem.* 1940, 5, 122.
14. For selected examples of catalytic asymmetric acetate aldol reactions, see: (a) Mikami, K.; Matsukawa, S. *J. Am. Chem. Soc.* 1994, 116. 4077. (b) Carreira, E. M.; Singer. R. A.; Lee, W. *J. Am. Chem. Soc.* 1994, 116. 8837. (c) For an overview, see: Carreira, E. M.; Fettes. A.; Marti, C. In Organic Reactions. Vol. 67; Overman. L. E., Ed.; Wiley & Sons: New York, 2006, 1-216; and references cited therein.
15. For selected reviews on organocatalysis, see: (a) List, B. *Chem. Rev.* 2007, 107, 5413. (b) MacMillan, D. W. C. *Nature* 2008, 455. 304.
16. For a recent review on Lewis base catalysis, see: Denmark, S. E.; Beutner, G. L. *Angew. Chem. Int. Ed.* 2008, 47, 1560; *Angew. Chem.* 2008. 120, 1584.

What is claimed is:

1. A catalyst compound represented by the structure (10A):

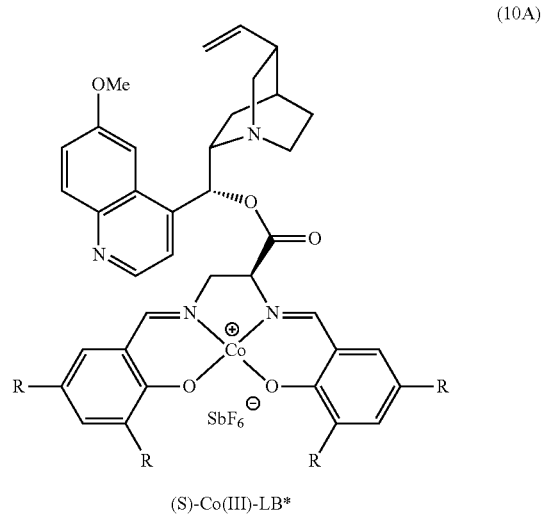

(10A)

(S)-Co(III)-LB* wherein one or more R moieties are: H, or branched or unbranched alkyl or aryl groups.

2. A catalyst compound represented by the structure (10):

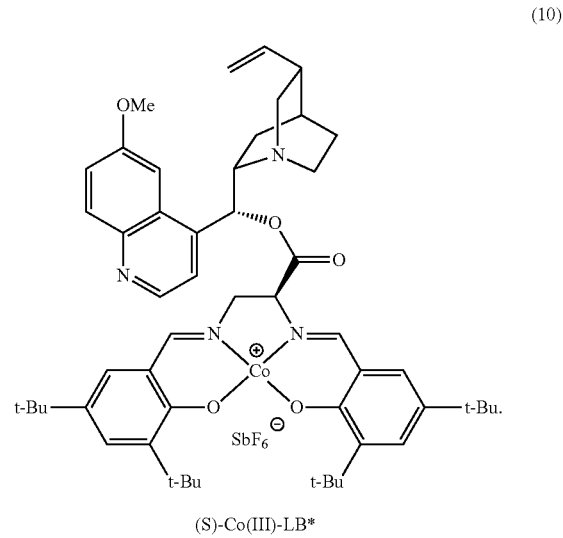

(10)

(S)-Co(III)-LB*

* * * * *